United States Patent
Wallace et al.

(10) Patent No.: US 11,412,926 B2
(45) Date of Patent: Aug. 16, 2022

(54) CORNEAL TOPOGRAPHY SYSTEM AND METHODS

(71) Applicant: Intelligent Diagnostics, LLC, Los Angeles, CA (US)

(72) Inventors: David A. Wallace, Los Angeles, CA (US); Stephen Klyce, Port Washington, NY (US); John R Rogers, Monrovia, CA (US); R Stephen Mulder, Tuscon, AZ (US); Mark A Kahan, Marlborough, MA (US); Paul E Glenn, Wellesley, MA (US)

(73) Assignee: Intelligent Diagnostics, LLC, Los Angeles, CA (US)

( * ) Notice: Subject to any disclaimer, the term of this patent is extended or adjusted under 35 U.S.C. 154(b) by 0 days.

(21) Appl. No.: 16/971,258

(22) PCT Filed: Feb. 22, 2019

(86) PCT No.: PCT/US2019/019178
§ 371 (c)(1),
(2) Date: Aug. 19, 2020

(87) PCT Pub. No.: WO2019/165227
PCT Pub. Date: Aug. 29, 2019

(65) Prior Publication Data
US 2020/0390327 A1    Dec. 17, 2020

Related U.S. Application Data

(60) Provisional application No. 62/635,462, filed on Feb. 26, 2018, provisional application No. 62/634,169, filed on Feb. 22, 2018.

(51) Int. Cl.
*A61B 3/107*    (2006.01)
*A61B 3/00*    (2006.01)
(Continued)

(52) U.S. Cl.
CPC ............ *A61B 3/107* (2013.01); *A61B 3/0008* (2013.01); *A61B 3/0041* (2013.01); *A61B 3/135* (2013.01); *A61B 3/152* (2013.01); *A61B 3/158* (2013.01)

(58) Field of Classification Search
CPC ..... A61B 3/107; A61B 3/0008; A61B 3/0041; A61B 3/135; A61B 3/152; A61B 3/158; A61B 5/00; A61B 3/12
(Continued)

(56) References Cited

U.S. PATENT DOCUMENTS 6,260,968 B1    7/2001    Stark et al.
10,842,373 B2 *    11/2020    Fink ..................... A61B 3/0033
(Continued)

FOREIGN PATENT DOCUMENTS

CN    202198572    4/2012
JP    H08266474    10/1996
(Continued)

OTHER PUBLICATIONS

International Search Report and Written Opinion of the International Searching Authority, dated May 15, 2019, PCT/US19/19178, 18 pages.
(Continued)

*Primary Examiner* — Mohammed A Hasan

(57) ABSTRACT

A mobile communication device-based corneal topography system includes an illumination system, a mobile communication device and a corneal topography optical housing. The illumination system is configured to generate an illumination pattern and to generate reflections of the illumination pattern off a cornea of a subject, wherein the illumination system is aligned along an axis of centers of the illumination pattern. The mobile communication device includes an image sensor to capture an image of the reflected
(Continued)

Smartphone-based corneal topography system illumination pattern. The corneal topography optical housing is coupled to the illumination system and the mobile communication device, wherein the corneal topography optical housing supports and aligns the illumination system with the image sensor of the mobile communication device. The corneal topography optical housing includes an imaging system coupled to the image sensor.

19 Claims, 16 Drawing Sheets

(51) Int. Cl.
  *A61B 3/135* (2006.01)
  *A61B 3/15* (2006.01)
(58) Field of Classification Search
  USPC ........................................................ 351/212
  See application file for complete search history.

(56) References Cited

U.S. PATENT DOCUMENTS

| | | |
|---|---|---|
| 2003/0009156 A1 | 1/2003 | Levine |
| 2005/0270484 A1 | 12/2005 | Maeda |
| 2011/0273669 A1 | 11/2011 | Abitbol |
| 2011/0299036 A1* | 12/2011 | Goldenholz ......... A61B 3/1208 351/206 |
| 2014/0063331 A1 | 3/2014 | GoldenBerg |
| 2014/0104574 A1 | 4/2014 | Grenon |
| 2014/0131055 A1 | 5/2014 | Cordani |
| 2014/0320811 A1 | 10/2014 | Wang et al. |
| 2015/0253647 A1 | 9/2015 | Mercado |
| 2016/0198946 A1 | 7/2016 | Zhou |
| 2017/0042421 A1* | 2/2017 | Wallace ................. A61B 3/135 |
| 2017/0087019 A1* | 3/2017 | Gonzalez ............... A61B 3/117 |
| 2017/0172406 A1 | 6/2017 | Pamplona |
| 2017/0181621 A1 | 6/2017 | Catanzariti et al. |
| 2017/0280994 A1 | 10/2017 | Kersting et al. |
| 2018/0092534 A1 | 4/2018 | Nabhan |
| 2019/0223714 A1 | 7/2019 | Raymond |

FOREIGN PATENT DOCUMENTS

| | | | |
|---|---|---|---|
| WO | WO 2012116807 | 9/2012 | |
| WO | WO 2016115285 | 7/2016 | |
| WO | WO2016/154558 | 9/2016 | |
| WO | WO-2016154558 A1 * | 9/2016 | ............... A61B 3/12 |
| WO | WO2016/179370 | 11/2016 | |
| WO | WO-2016179370 A1 * | 11/2016 | ............... A61B 3/12 |
| WO | WO 2017031019 | 2/2017 | |

OTHER PUBLICATIONS

"An Accessible Approach for Corneal Topography", De Rosa, Dec. 2013.
U.S. Appl. No. 17/591,953, Office Action dated Mar. 30, 2022.
European Extended Search Report Including Search Report and Search Opinion, dated Feb. 17, 2022, Application No. EP 19 75 6988, 14 pages.

* cited by examiner (a) Prototype model (b) Plain prototype model

Smartphone-based corneal topography system

CORNEAL TOPOGRAPHY SYSTEM AND METHODS

RELATED APPLICATIONS

This application claims priority to PCT Application No. PCT/US2019/019178, filed on Feb. 22, 2019, U.S. provisional patent application Ser. No. 62/634,169, filed Feb. 22, 2018, entitled "Smartphone-Based Corneal Topography System," and U.S. provisional patent application Ser. No. 62/635,462, filed Feb. 26, 2018, entitled "Smartphone-Based Corneal Topography System," the entire disclosures and content of which are all hereby incorporated by reference and assigned to the same Assignee and/or Applicant.

BACKGROUND

Prior approaches to corneal topography can be less than ideal in at least some instances. For example, many commercially available corneal topography systems are larger than would be ideal, which can make it somewhat cumbersome and expensive for health care professionals who need to provide dedicated space for these systems, and such devices may not be readily integrated into an exam room in at least some instances. Although efforts have been made to decrease the size of corneal topography systems, such devices have provided less than ideal results in at least some instances. For example, although smart phone based corneal measurement systems have been proposed, in at least some instances such devices may not measure corneal topography and may merely provide qualitative rather than quantitative information in at least some instances. Alignment of the eye with the corneal topography system can be helpful for obtaining accurate corneal topography measurements, and at least some of the prior approaches may have less than ideal alignment and accuracy in at least some instances.

Prior art corneal topography systems (which may be connected to a laptop computer or a desktop computer) project an image of Placido rings off of a cornea of a human eye and into a digital imaging sensor (or one or more digital imaging sensors). Some prior art systems are affixed to a desktop computer or may attach to a laptop computer, each of which may be typically running a Windows operating system or a MAC operating system. Prior art desktop-based or laptop-based corneal topography systems may use an image sensor and a custom, proprietary imaging lens system designed to suit the desired parameters of the instrument including field of view, focal length, and desired image magnification to maximize use of the target commercial image sensor for its intended purpose. The prior art desktop-based or laptop-based corneal topography systems do not require telescope optics because they utilize custom or proprietary imaging lens systems which provide the desired field of view and imaging magnification for the image sensor. For example, the Nidek OPD-III desktop topography systems may incorporate a Placido ring outside diameter of approximately 22 mm (horizontal)×19 mm (vertical), and a focal distance of approximately 70 mm (from the front lens of their imaging system).

A prior art corneal topography system attached to a smartphone is described in "An Accessible Approach to Corneal Topography" by Andre Luis Beling da Rosa ("Beling da Rosa publication") in December of 2013. The article describes a clip-on device with three layers: 1) an illumination layer to provide illumination of concentric rings; 2) a support layer helping with the image captured using a lens and also with the diffusion and 3) the pattern layer (which gives a shape to projected patterns). FIG. 1 illustrates a smartphone clip-on corneal topography device having three layers according to the prior art as shown in pages 40 and 41 of the Beling da Rosa publication. Another prior art corneal topography system attached to a smartphone is described in "Design And Development Of An Ultraportable Corneal Topographer For Smartphones As A Low Cost New Tool For Preventing Blindness Caused By Keratoconus" by Pinheiro et al ("Pinheiro publication"). This device includes a support cover, a printed circuit board with LEDs (light emitting diodes), an optical system for magnification, a cone with transparent and black concentric rings (principle of Placido) and a dome. However, the Pinheiro publication does not describe any details of an optical system.

Prior art corneal topography systems incorporated linear imaging, meaning that the prior art corneal topography systems projected an image in a straight line concentric with a ray entering an exact center of a Placido illumination system, which was perpendicular to a plane of concentric rings. However, none of these prior art corneal topography systems folded the beam back utilizing mirrors in an optical bench assembly or corneal topography optical housing.

In light of the above, improved corneal topography devices are needed that will overcome at least some of the aforementioned disadvantages of the prior art.

SUMMARY

In some embodiments, the mobile communication device-based corneal topography system and methods can provide decreased size and accurate topography measurements, such the system can be readily utilized by health care professionals. The topography system may comprise one or more components of a commercially available smart phone, such that the size, cost and complexity of the device can be decreased. These components can be configured to provide improved alignment, and can be arranged to facilitate measurements and improve alignment to improve the accuracy of measurements.

In some embodiments, the mobile communication device-based corneal topography system may be a small device that is easily transportable, which allows the system to be utilized in many locations. The mobile communication device-based corneal topography system may be mounted on a slit-lamp microscope. In some embodiments, the topography system comprises batteries and is configured to be powered by batteries to decrease size and increase mobility.

As a slit-lamp microscope mounted instrument, the mobile communication device-based corneal topography system may be able to capture data with high z-axis precision, and thus enable very precise optical power calculation. Thus, the mobile communication device-based corneal topography system's corneal power measurement accuracy may be equal to or better than prior art desktop-mounted corneal topography system, and much better than any existing hand-held or portable corneal topography system. In some embodiments, the mobile communication device-based corneal topography system may improve alignment significantly as compared to prior systems.

In some embodiments, a mobile communication device-based corneal topography system, an illumination system, a mobile communication device, and a corneal topography optical housing. The illumination system generates an illumination pattern (e.g., concentric rings) and generate reflections of the illumination pattern off a cornea of a subject. The mobile communication device includes an image sensor to capture an image of the reflected illumination pattern such as concentric rings, and the corneal topography is determined or calculated in response to the image. In some embodiments, the illumination pattern may be a predetermined illumination pattern. The corneal topography housing is coupled to both the illumination system and the mobile communication device and the corneal topography optical housing and supports and aligns the illumination system with the image sensor of the mobile communication device. In some embodiments, the illumination system is aligned along an axis of the centers of the illumination pattern. In some embodiments, the corneal topography optical housing includes an optical system having a Keplerian configuration to magnify the image of the reflected concentric rings being evaluated, so as to take maximum advantage of a sensor area of the image sensor of the mobile computing device and also to decrease an optical path length between the cornea of the subject and the image sensor. In some embodiments, the corneal topography optical housing may be mounted on a slit lamp microscope.

In some embodiments, a mobile communication device-based corneal topography system may include an illumination system, a mobile communication device, and a corneal topography optical housing. Although reference is made to a Placido illumination system, other illuminations can be used, such as discrete points of light from discrete light sources in a predetermined pattern, and rectilinear grids. The illumination system may generate an illumination pattern and also generate reflections of the illumination pattern off a cornea of a subject. The mobile communication device may include an image sensor to capture an image of the illumination pattern. In some embodiments, the corneal topography optical housing may include or house two or more mirrors, the two or more mirrors being positioned in an image path of the reflected illumination pattern image and located in front of a position of the image sensor of the mobile communication device. In some embodiments, the two or more mirrors may reduce a distance between the subject's cornea and the camera of the mobile communication device as compared to a system utilizing a corneal topography optical housing without the two or more mirrors. The reflective mirrors can decrease the overall size of the topography device and increase portability of the system. In some embodiments, the two or more mirrors in the image path of the reflected concentric ring image may reduce a distance between the subject's cornea and the camera of the mobile communication device to less than 165 millimeters (or 6.5 inches). In some embodiments, the two or more mirrors in the image path of the reflected concentric ring image may reduce a distance between the subject's cornea and the camera of the mobile communication device ranging between 50 millimeters to 165 millimeters (or 2 to 6.5 inches). In some embodiments, the two or more mirrors in the image path of the reflected concentric ring image may reduce a distance between the subject's cornea and the camera of the mobile communication device ranging between 165 millimeters to 204 millimeters (or 6.5 inches to 8 inches). In some embodiments, the corneal topography optical housing may have a length to keep a distance between the examiner's eye and the subject's eye between approximately 304 to 356 millimeters (or 12 and 14 inches). In some embodiments, the corneal topography optical housing may have a length to keep a distance between the examiner's eye and the subject's eye between approximately 254 to 381 millimeters (or 10 and 15 inches).

In some embodiments, a mobile communication device-based corneal topography system may include an illumination system, a mobile communication device and a corneal topography optical housing. The illumination system may generate an illumination pattern which may be reflected off a subject's cornea. The mobile communication device may comprise an image sensor to capture an image of the reflected illumination pattern. In some embodiments, a surface of the corneal topography optical housing that is coupled to the mobile communication device may be tilted with respect to a vertical axis. In some embodiments, a surface of the mobile communication device may be tilted with respect to the vertical axis to provide enhanced viewing of the reflected concentric rings image by an examiner or user. In some embodiments, the surface of the corneal topography optical housing may be tilted between 1 to 40 degrees with respect to the vertical axis. In some embodiments, the surface of the mobile communication device may be tilted between 0 to 40 degrees with respect to the vertical axis. In some embodiments, the surface of the corneal topography optical housing and/or a surface of the mobile communication device may be tilted between 0 to 10 degrees with respect to the vertical axis. In some embodiments, the optical axis of the illumination system and the corneal topography system may be tilted with respect to horizontal in order to provide ease of use and less eye strain on the subject being examined. In some embodiments, the optical axis may be inclined downward moving away from the eye and the display or screen of the mobile communication device may be inclined upward as viewed by a user.

In some embodiments, a mobile communication device-based corneal topography system may include an illumination system, a mobile communication device and/or a corneal topography optical housing. The illumination system may generate an illumination pattern which may be reflected off a cornea of a subject. The mobile communication device may comprise an image sensor to capture the image of the reflected illumination pattern. In some embodiments, the corneal topography optical housing may include or house two or more mirrors, where the two or more mirrors may be located in an image path of the reflected illumination pattern image, and the angle of inclination of the two or more mirrors in an image path of the image results in the image of the reflected being tilted by an angular displacement with respect to the vertical axis to improve viewing of the reflected illumination pattern image by an examiner. In some embodiments, the angular displacement of the reflected illumination pattern image ranges between 0 and 15 degrees. In some embodiments, the angular displacement of the reflected illumination pattern image ranges between 0 and 40 degrees.

In some embodiments, a mobile communication device-based corneal topography system includes an illumination system, a mobile communication device, and a corneal topography optical housing. The illumination system may generate an illumination pattern, which may be reflected off a cornea of a subject and may also include an eye piece. The mobile communication device may include an image sensor that captures an image of the reflected illumination pattern. In some embodiments, the illumination system may be tilted upward by an angle of inclination with respect to a horizontal axis to provide more comfortable viewing by a subject being examined. In some embodiments, the angle of inclination of the illumination system and eye piece ranges from 0 to 7 degrees. In some embodiments, the angle of inclination of the illumination system and/or eye piece ranges from 0 to 15 degrees.

In some embodiments, a mobile communication device-based corneal topography system includes an illumination system, a mobile communication device, and a corneal topography optical housing. The illumination system may generate an illumination pattern, which may be reflected off a cornea of a subject. The mobile communication device may include an image sensor that captures an image of the reflected illumination pattern. In some embodiments, the illumination system, the corneal topography optical housing and the mobile communication device may be positioned to maintain a horizontal plane of alignment between a subject's eye and an examiner's eye during operation of the mobile communication device-based corneal topography system. In some embodiments, the corneal topography optical housing may be coupled to a slit lamp microscope. In some embodiments, the coupling of the slip-lamp microscope to the corneal topography optical housing provides +/−100 micron z-axis positional accuracy which results in +/−0.25 Diopter accuracy in calculating accurate corneal power.

In some embodiments, a mobile communication device-based corneal topography system includes an illumination system, a mobile communication device, and a corneal topography optical housing. The illumination system may generate an illumination pattern, which may be reflected off a cornea of a subject. The mobile communication device may include an image sensor that captures an image of the reflected concentric rings. In some embodiments, the corneal topography optical housing includes a first mirror and a second mirror positioned in an image path of the reflected illumination pattern image. In some embodiments, the first mirror may be a partial reflectance, partial transmittance mirror and a fixation light source may be located behind the first mirror. In some embodiments, the fixation light source may be positioned behind the partial reflectance, partial transmittance mirror to allow a subject being examined to focus on the fixation light source. In some embodiments, the system may further include an autorefractor and the second mirror is a partial reflectance, partial transmittance mirror. In some embodiments, the autorefractor may be positioned behind the second mirror to measure aberrations in the subject's by analyzing the reflected illumination pattern image.

In some embodiments, a mobile communication device-based corneal topography system includes a illumination system, a mobile communication device, and a corneal topography optical housing. The illumination system may generate an illumination pattern, which may be reflected off a cornea of a subject. The mobile communication device may include an image sensor that captures an image of the reflected illumination pattern. In some embodiments, the illumination system may comprise two or more proximity sensors which are located on opposite sides of a plastic cylinder that forms the illumination system. In some embodiments, the two or more proximity sensors may generate signals when a subject is being examined. In some embodiments, comparison circuitry may compare amplitudes of the generated signals received from the two or more proximity sensors and computer-readable instructions executable by one or more processors may receive the comparison of the amplitudes of the generated proximity sensor signals to determine whether a left eye or a right eye of a subject is being examined.

In some embodiments, a mobile communication device-based corneal topography system includes an illumination system, a first mobile communication device, and a first corneal topography optical housing. The illumination system may generate an illumination pattern, which may be reflected off a cornea of a subject. The first mobile communication device may include an image sensor that captures an image of the reflected image pattern the image sensor is located at a first position on a back surface of the first mobile communication device. In some embodiments, the first corneal topography optical housing may include two or more mirrors to create an image path to reflect the captured image into a center axis of the first position of the image sensor. In some embodiments, a second mobile communication device may include an image sensor, the image sensor being located in a second position on a second position on a back surface of the second mobile computing device. In some embodiments, the second corneal topography housing includes two or more mirrors to create an image path to reflect the captured image onto a center axis of the second position of the image sensor of the second mobile communication device.

In some embodiments, a mobile communication device-based corneal topography system includes an illumination system, the illumination system configured to generate an illumination pattern and to generate reflections of the illumination pattern off a cornea of a subject, wherein the illumination system is aligned along an axis of centers of the illumination pattern. The system also includes a mobile communications device, the mobile communications device comprising an image sensor, the image sensor to capture an image of the reflected illumination pattern; and a corneal topography optical housing coupled to the illumination system and coupled to the mobile communication device, wherein the corneal topography optical housing supports and aligns the illumination system with the image sensor of the mobile communication device. In some embodiments, the corneal topography optical housing comprising an imaging system coupled to the image sensor. In some embodiments, the imaging system further comprising a Keplerian configuration to magnify the image of the reflected illumination pattern being evaluated and also to decrease an optical path length between the cornea of the subject and the image sensor. In some embodiments, the imaging system comprises two or more mirrors, the two or more mirrors being positioned in an image path of the reflected illumination pattern image and located in front of a position of the image sensor of the mobile communication device. In some embodiments, a surface of the mobile communication device is tilted with respect to the vertical axis to provide enhanced viewing of the reflected illumination pattern image by the examiner. In some embodiments, the mobile communication device-based corneal topography system of claim 1, the imaging system comprises two or more mirrors and the two or more mirrors are titled with respect to a vertical axis and/or a horizontal axis. In some embodiments, the illumination system is titled upward by an angle of inclination with respect to a horizontal axis to facilitate alignment with an eye of a subject being examined. In some embodiments, the illumination system, the corneal topography optical housing and the mobile communication device are positioned to maintain a horizontal plane of alignment between a subject and an examiner's during operation of the corneal topography system. In some embodiments, the corneal topography housing further comprising a first mirror and a second mirror, the first mirror and the second mirror being partial reflectance mirrors. In some embodiments, the system further comprises two or more proximity sensors, the two or more proximity sensors coupled to the illumination system and utilized to determine whether a left eye or a right eye of the subject is being examined.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

The patent or application file contains at least one drawing.

A better understanding of the features, advantages and principles of the present disclosure will be obtained by reference to the following detailed description that sets forth illustrative embodiments, and the accompanying drawings of which are described below.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Figure 1:
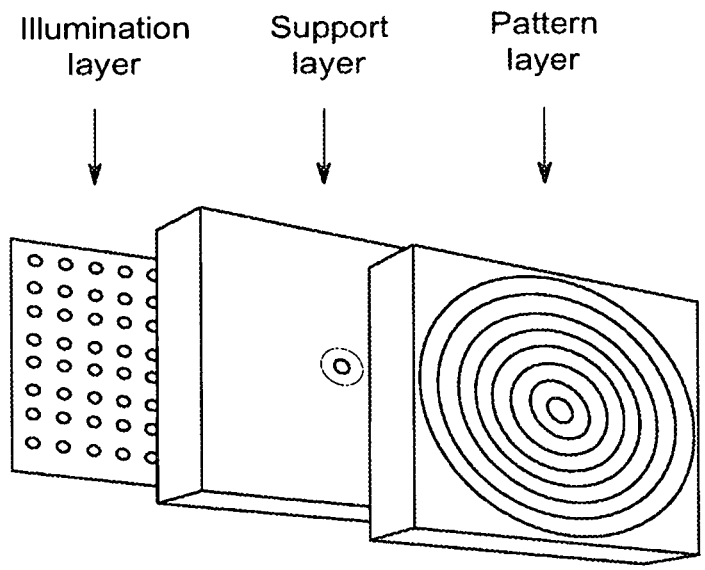
FIG. 1 illustrates a smartphone clip-on corneal topography device having three layers according to the prior art.
Figure 1:
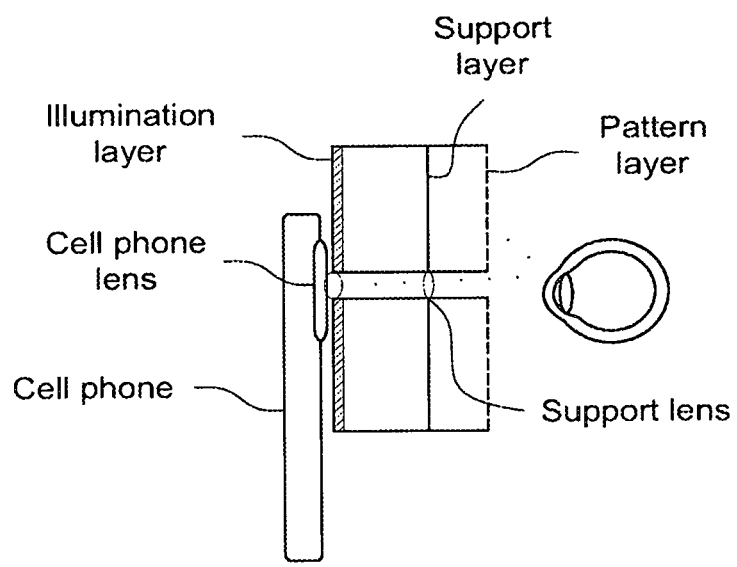
Figure 2A:
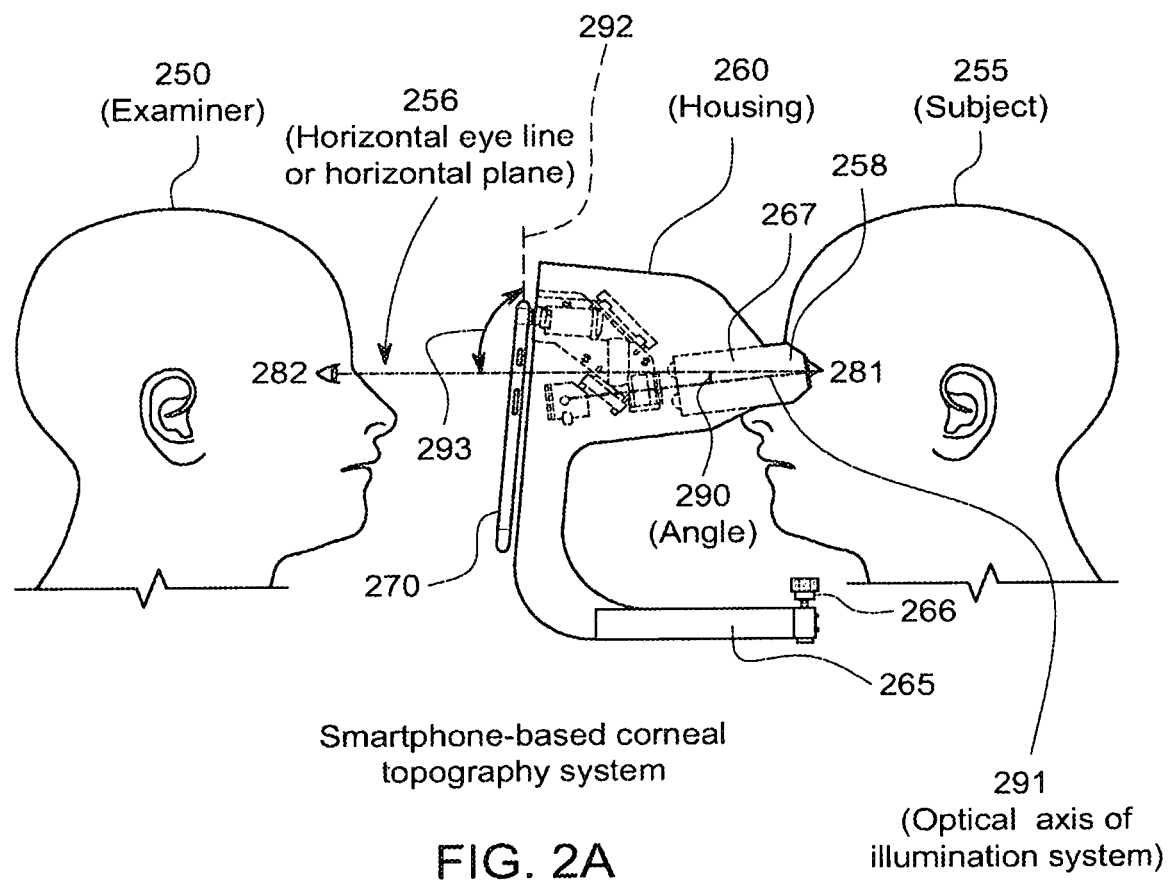
FIG. 2A illustrates a mobile communications device-based corneal topography system according to some embodiments.

FIG. 2A illustrates a mobile communication device-based corneal topography system according to some embodiments. The mobile communication device corneal topography system may comprise a mobile communication device 270 and a corneal topography optical housing 260. In some embodiments, the below listed components (along with optical components) may be contained in the corneal topography optical housing 260. In some embodiments, the optical housing 260 may include, or have contained therein, one or more optical components or assemblies (lenses, mirrors, optical pipes or tubes, light sources), one or more processors, communication circuitry, one or more memory devices, one or more power sources, computer-readable instructions stored in the one or more memory devices and executable by one or more processors, a mounting assembly 265 including a slit-lamp mounting post 266 and a pattern (e.g., Placido ring) illumination system 267. The mobile communications device-based corneal topography system record keratoscopic images of the cornea and includes dedicated software (referred to hereinafter as corneal topography software). In some embodiments, the corneal topography software digital processes, displays and stores keratoscopic images, which are utilized to generate or produce a topographical map of the cornea. In some embodiments, the topographical map represents the surface of the cornea by highlighting the curvature by means of a colorimetric scale, i.e. a certain color corresponds to a determined interval of values of the surface's curvature radius.

In order to acquire an corneal image, the patient is asked to place his/her chin and forehead comfortably against the chin and forehead rest of a slit lamp microscope to which the mobile-computing device-based corneal topography system is mounted, and to observe the luminous target so that it is in the center of the innermost light ring of the placido rings. The operator moves the keratoscope until he recognizes that the patient is aligned along the X, Y and Z axes. In this context, X is the horizontal axis, Y is the vertical axis and Z is the distance from the camera's correct focal plane to the corneal vertex. In some embodiments, the operator presses the joystick button and the mobile computing device camera acquires the corneal image, which is displayed on the screen of the mobile computing device executing the corneal topography application software. In some embodiments, the corneal topography system software processes the video image of the cornea to create a data file. In some embodiments, the data file and the Placido rings image are then uploaded securely to cloud-based servers, which are HIPAA and GDRP-compliant. In some embodiments of the mobile computing device-based corneal topography system, an examiner or user's eye may be in horizontal plane (or within +/−10 degrees) or an eye line or a patient or subject (which is illustrated by reference number 256 in FIG. 2A). In some embodiments, a mobile communication device may be tilted slightly with respect to a vertical axis to allow for ease of use by the examiner or user. Reference number 292 illustrates a tilting of the mobile communication device surface. In FIG. 2A, reference number 293 illustrates an angle between a horizontal eye line 256 and a tilt of the mobile communication device 292. In some embodiments, an optical axis of the illumination system may be tilted downward with respect to horizontal axis. In some embodiments, the horizontal axis may be illustrated by reference number 291. This may provide a more comfortable position for the subject being examined. In FIG. 2A, reference number 290 illustrates an angle between a horizontal eye line 256 and the optical axis 291 of the illumination system The terms smartphone, mobile phone, mobile computing device, portable computing device, mobile communications device and portable communications device may be utilized interchangeably through the specification. For example, a mobile communication device (and the other devices mentioned above), may refer to a device or apparatus that comprises one or more processors, one or more memory devices, communication circuitry (such as wired or wireless communication transceivers), a display or screen, a power source, a power source interface, one or more sensor assemblies and/or one or more image sensors. In some embodiments, one or more image sensors may be one or more cameras, CCD arrays or similar devices. The mobile communication device may also comprise computer-readable instructions stored in the one or more memory devices that are executable by the one or more processors to perform certain features or functions as described herein.

Figure 2B:
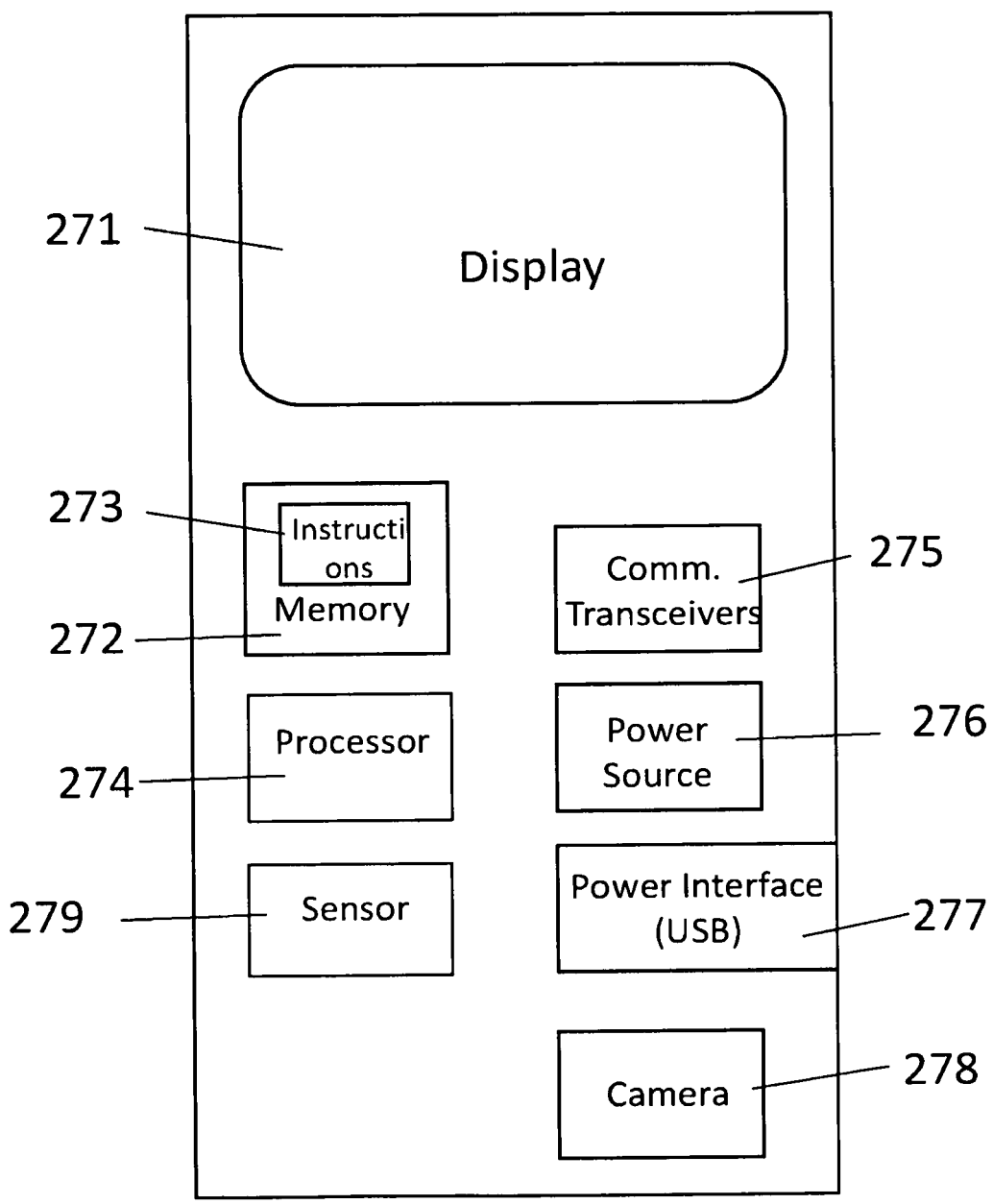
FIG. 2B illustrates a mobile communication device utilized in the corneal topography system according to some embodiments.

FIG. 2B illustrates a mobile communication device utilized in the corneal topography system according to some embodiments. In some embodiments, the mobile communication device 270 may comprise one or more displays or screens 271, one or more memory devices 272, one or more processors 274, communication circuitry 275 such as one or more communication transceivers, one or more power sources 276, one or more power interfaces 277, one or more sensor assemblies 279 and/or one or more cameras 278. In some embodiments, computer-readable instructions 273 executable by the one or more processors 274 generate and operate the corneal topography application software (and features included therein) utilized by the examiner to interface with and examine the patient or subject. In some embodiments, computer-readable instructions 273 executable by the one or more processors 274 interface with components and assemblies of the mobile communication device 270 as well as components and assemblies within the corneal topography optical housing 260. In some embodiments, the one or more displays or screens 271 present corneal images and other images associated therewith along with input screens for the corneal topography application software. In some embodiments, the one or more display screens 271 may comprise touch screens (which receive input from stylus, on screen keyboards, etc.), as well as to receive input from other input devices. In some embodiments, the one or more memory devices 272 may store the computer-readable instructions 273 discussed above, operating system software for the mobile communication device 270, and/or parameters or settings for the mobile communications device 270. In some embodiments, the one or more processors 274 may be mobile device processors and/or controllers and may be coupled to the one or more memory devices 272, the one or more displays 271, the communication circuitry 275, the one or more power sources 276, the power interface 277, the one or more sensor assemblies 279 and/or the one or more image sensors or cameras 278. In some embodiments, the communication circuitry 275 may comprise one or more wireless communication transceivers and/or one or more wired communication transceivers. In some embodiments, the one or more wireless communication transceivers may comprise one or more personal area network (PAN) transceivers (e.g., Bluetooth, Bluetooth Low Energy, Zigbee transceivers), wireless LAN (e.g., WiFi and/or 802.11 transceivers), and/or cellular transceivers (e.g., 3G, 4G, and/or 5G based transceivers). In some embodiments, the communication circuitry 275 may allow the mobile communication device 270 to communicate with, transmit to and/or receive information from the corneal topography optical housing 260. In addition, the communication circuitry 275 may allow the mobile communication device 270 to communicate with external computing devices such as other computing devices in an examiner's office and/or remote computing devices or servers (e.g., cloud-based servers). In some embodiments, the one or more power sources 276 may be one or more rechargeable batteries. In embodiments, the power interface 277 may be coupled to the one or more power sources 276. In embodiments, the power interface 277 may be a USB interface that provide power to the power source as well as a wired communication interface from an external power source (e.g., an AC adapter, a computing device, etc.). In some embodiments, the mobile communication device 275 may comprise one or more sensor assemblies 279. In embodiment, the one or more sensors assemblies may comprise a GPS sensor, one or more accelerometers, and/or one or more gyroscopes. In some embodiments, the mobile communication device 270 may comprise one or more cameras or image sensors 278. In embodiments, the one or more cameras or image sensors 278 may capture reflected images of a patient's cornea and the captured corneal image may be communicated, utilizing the one or more processors 274, to the one or more displays 271 of the mobile communication device 270.

Figure 2C:
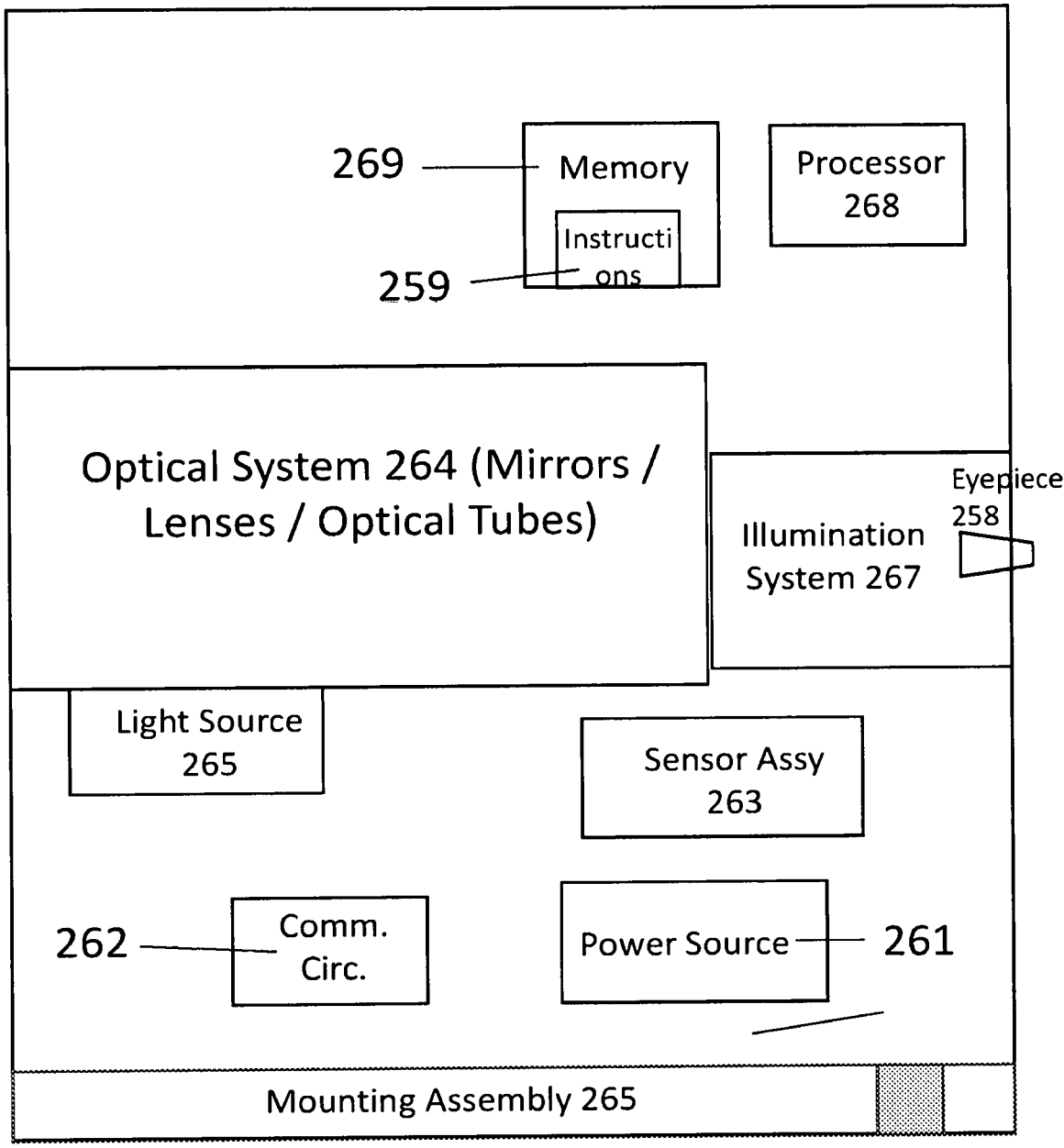
FIG. 2C illustrates a corneal topography optical housing in the corneal topography system according to some embodiments.

FIG. 2C illustrates a corneal topography optical housing 260 in the corneal topography system according to some embodiments. In some embodiments, a corneal topography housing 260 may comprise a mounting assembly 265, communication circuitry 262, one or more power sources 261, one or more sensor arrays 263, one or more light sources 265, one or more memory devices 269, one or more processors 268, an illumination system 267 (e.g., a Placido illumination system), an eye piece 258, and/or an optical assembly 264 (e.g., one or more mirrors, lenses, and/or lens barrels). In some embodiments, computer-readable instructions 259 may be stored in one or more memory devices 269 and may be executable by one or more processors 268 to control operations of the components or assemblies in the corneal topography housing 260. In some embodiments, the mounting assembly 265 may be utilized to connect or couple the corneal topography optical housing 260 to another device (e.g., a slit lamp microscope). In some embodiments, the mounting assembly may be connected to the slit-lamp microscope via a positioning pin or mounting post 266. In some embodiments, the positioning may be placed in a hole concentric with the axis of rotation of the slit beam illumination system, and the pivot-point of the binocular microscope. In some embodiments, the slit lamp may also incorporate a chin rest and forehead rest that helps stabilize the subject's head, minimizing needed movement of the optics head during examination.

In some embodiments, the corneal topography optical housing 260 may comprise communication circuitry 262, which may comprise wireless communication transceivers and/or wired communication transceivers. In some embodiments, the wireless communication transceivers may comprise PAN transceivers (Bluetooth, BLE, Zigbee) and/or wireless LAN transceivers (e.g., WiFi or 802.11 transceivers). In some embodiments, the corneal topography optical housing 260 may comprise one or more sensor assemblies 263, which may comprise proximity sensors. In some embodiments, the corneal topography optical housing may comprise an eye piece 258. In some embodiments, the examination subject can place one of their eyes in the eyepiece 258 in order to start the examination. In some embodiments, the corneal topography optical housing 260 may comprise one or more light sources 265. In some embodiments, the one or more light sources 265 may comprise a fixation light source which may generate a fixation beam. In some embodiments, the subject or patient being examined may focus their gaze on, or look at the fixation beam. In some embodiments, the corneal topography optical housing may comprise an illumination system 267 such as a Placido illumination system which illuminates Placido rings. In some embodiments, the Placido rings are reflected off the subject or patient's cornea. Although this disclosure refers to utilizing Placido rings and thus a Placido illumination system, other patterns may be utilized and reflected off a patient's cornea in order to be utilized in analyzing corneal topography. In some embodiments, an illumination system may generate an illumination pattern.

In some embodiments, the corneal topography optical housing 260 may comprise an optical subassembly or optical system 264. In some embodiments, the optical subassembly or system 264 may transmit or reflect a corneal image and/or a Placido rings image to the one or more cameras or image sensors in the mobile communication device 270. In some embodiments, the optical subassembly or optical system 264 may comprise one or more mirrors, one or more lenses and/or one or more lens barrels.

A mobile communication device optical system may an objective lens, having collimated (or nearly collimated) light on one side, and an image on another side. A mobile communication device may comprise one or more components of an iPhone®, an Android® phone, a Windows® phone, or other similar devices. A mobile communication device optical system may have a short focal length (about 6.6 millimeters). For the purposes of this specification, an aperture stop of an optical system is an aperture that limits the diameter of an on-axis or off-axis ray bundle, and a pupil of a system is an image of the aperture stop. An entrance pupil of a system (such as a mobile computing device) is an image of the aperture stop as seen by an observer looking into the system from an object side (rather than from a sensor side). Having defined the entrance pupil, it is also possible to define an exit pupil, i.e., an image of an aperture stop, as seen from a sensor side of an optical system. The two pupils are both images of the aperture stop; as a consequence, they are images of each other.

In embodiments, a mobile communication device-based corneal topography system may be an "add-on" to a mobile communication device, such that mires of a Placido assembly may be imaged to a sensor (e.g., an image sensor) of the mobile communication device. In embodiments, a mobile communication device-based corneal topography system may be designed to "mate to", or work together with, a mobile communication device in such a way that a correct field of view may be obtained and that a corneal image is acceptably sharp over the field of view in question. Thus, the mobile communication device lens and a mobile communication device-based corneal topography system may each be subsystems of the overall optical system that images the mires to a mobile communication device image sensor.

For the two subsystems (e.g., the mobile communication device lens and mobile communication device-based corneal topography optical system) to work well together, several key requirements may need to be met: (a) Collimation; (b) Field of view; (c) Pupil matching; and/or (d) aberration correction. Since a mobile communication device is designed to receive light that is collimated or close to collimated, a mobile communication device-based corneal topography system may provide light that is collimated (or nearly so) in a space immediately upstream from the mobile communication device. In embodiments, since an object of the mobile communication device-based corneal topography system (e.g., the mires of a Placido assembly) are not at infinity but lie at a finite distance from the mobile communication device, the mobile communication device-based corneal topography system may be viewed, functionally as a collimator operating over a finite field of view. In embodiments, mires may be defined as one of the test objects in the mobile communication device-based corneal topographer; its image (also called a mire), which is mirrored on the corneal surface, may be measured to determine a radii of curvature of the cornea. In some embodiments, Placido assemblies or Placido illumination systems may project a series of concentric rings of light on the anterior corneal surface of a subject's eye. From a standpoint of optical design, a collimator may be raytraced in the reverse direction, e.g., from a collimated space toward an image located, in this case, at the mires of the Placido assembly (e.g., such as a Placido cone). It is worth noting that in some embodiments, a mobile communication device-based corneal topography system has collimated light on one side and an image (or an object, depending on the direction of the raytrace) on the other side. As mentioned, although this specification may specifically refer to a Placido illumination system that generates concentric rings, the subject matter described herein also applies to other illumination systems that generate other illumination patterns.

In some embodiments, another requirement of a mobile communication device-based corneal topography system is that a required field of view (FOV) may be covered without any important part of a corneal image being obscured. Because this may be (except for two folding mirrors) an on-axis optical system with a reflection at a subject's cornea, some small amount of central obscuration is unavoidable. This small amount of central obscuration leads to a small region on the cornea in which a corneal topography cannot be measured. It is an important feature of any mobile communication device-based corneal topography system that a diameter of an unmeasurable region of a central cornea be minimized. Minimizing a size of an unmeasurable region may require that a size of a hole in a Placido assembly (e.g., a Placido cone) be minimized, so that the diameter of an innermost ring as seen reflected in the cornea, may be as small as possible. Minimizing a diameter of a hole may require, in practice, that a pupil (an image of an aperture stop) be located at the hole. If this is done, then the various beams for the various mire locations all cross each other at this location. By crossing at this location, the various beams for the various mire locations may collectively share a same physical space, i.e., the hole need only be sized to be large enough to pass a single beam from a single mire location, and as a result, all of the beams from all of the mire locations may pass through the same hole.

For the two optical subsystems to work together, a pupil of the mobile communication device-based corneal topography system should be located at or close to the entrance pupil of the mobile communication device. This is for reasons that are analogous to the discussion above. If the beams exiting a mobile communication device-based corneal topography system are all to enter the mobile communication device, and if (for reasons of light-collection efficiency), the beams are all to be of maximum possible diameter, then the beams should all be a same diameter as the mobile communication device entrance pupil, and the beams must all cross each other at that location so that they all share that same location in space. If the beams did not share the same location in space, then the displaced beams would require that entrance pupil diameter be enlarged. Since that is not possible, the result would be that the beams be either partially or entirely blocked by the aperture stop of the mobile communication device.

Thus, as described in the two paragraphs above, a mobile communication device-based corneal topography system may be required to have a pupil at a hole of a Placido assembly (e.g., a Placido cone, disc, parabola, or cylinder) and a pupil at a mobile communication device lens. A simple, no-additional-optics solution to this problem may be to place a mobile communication device camera (or image sensor) directly at a hole in the Placido assembly (e.g., the Placido cone). While this is a simple solution, this solution would not satisfy the field of view requirements of the mobile communication device-based corneal topography system. Specifically, a mobile communication device lens (e.g., even a so-called "telephoto" lens), is designed to cover a wider field of view than is desired in the mobile communication device-based corneal topography system. As a result, if this simple solution were adopted, a direct image of the eye (e.g., cornea and surrounding area) would occupy a small region near a center of the mobile communication device sensor, and the images of the mires, as reflected in the cornea, would occupy an even smaller region. The mire images would be quite thin, and inadequate sampling by the mobile communication device pixels would result.

To avoid the problems described above for the no-additional-optics solution, the mobile communication device-based corneal topography system may be designed or configured with additional optics to magnify the image, (i.e., to map a smaller field of view to an image sensor of the mobile communication device). Accordingly, the mobile communication device-based corneal topography system requirements described thus far may be that: (1) An object—the mires of the Placido assembly (e.g., Placido cone)—may be collimated (e.g., imaged to infinity) in order to be viewed by another system (in this case the mobile communication device optical system that expects its object to be located at infinity); (2) The mobile communication device-based corneal topography system may have an exit pupil located at the entrance pupil of the second optical system, the mobile communication device; and (3) The mobile communication device-based corneal topography system may have a real image of the pupil, in this case located at or near a hole in the Placido assembly (e.g., Placido cone) or illumination system.

These requirements are similar to those of a surgical or dental loupe. Such magnifying systems exist in both "Keplerian" and "Galilean" forms or configurations. The names for Keplerian and Galilean loupes derive from the names of similar telescope designs. The principal difference between a surgical loupe and a telescope is that telescopes are understood to have objects located at infinity, whereas surgical loupes are designed for objects at a finite distance, typically less than a meter. With both telescopes and loupes, the "Keplerian" design form or "Keplerian configuration" may comprise two lenses or groups of lenses having positive power and an internal image between them, whereas the "Galilean" form or configuration comprises one lens or group of lenses containing positive power and another lens or group of lenses having negative power, with no internal image. Of these two design forms or configurations, only the Keplerian design form or configuration has a real exit pupil. The Galilean design form or configuration typically has an aperture stop located at the front lens group, and no image of this stop (no exit pupil) is formed after the last lens of the system. ("Opera glasses" are an example of a Galilean telescope.) As a consequence of there being no real exit pupil formed at the entrance pupil of the secondary imaging system—at the eye pupil, in the case of opera glasses—the field of view is limited to a fraction of what is available with the Keplerian design form or configuration. An alternative analysis of the same Galilean system is possible: one may consider the pupil of the eye to be the "aperture stop" of the Galilean system. In this case no image of this stop (no pupil) is formed at the front lens, and the field of view is limited by the outer diameter of the front lens. Therefore, the result is the same.

By virtue of having two positive lens groups and an internal image, an optical system including a Keplerian design form or Keplerian configuration (e.g., a Keplerian loupe optical system) creates a real image of an aperture stop. In a telescope, one pupil falls at the eye and the other pupil falls at the front lens group (one of these may be considered to be the aperture stop and the other its image). Either way, the eye pupil is imaged to the front lens group, and the diameter of the front lens group does not restrict the field of view of the system.

For many visual magnification applications, the Galilean design form or configuration has the advantage of providing an "upright" image. The Keplerian design form or configuration provides an "inverted" image unless the image is inverted a second time, for instance using a prism system. Most commercial binoculars are of a Keplerian design form or configuration with an image-inverting prism located between the objective lens and the eyepiece in each of the two eye channels. Likewise, Keplerian loupes incorporate an image-inverting prism in each of the assemblies for the two eyes.

For the application of a mobile computing device-based corneal topographer system, it is not necessary to provide an "upright" image, as the image is collected by a digital image sensor and may be electronically "inverted" before being displayed to the user. For this reason, there is no drawback to using an optical system including a Keplerian design form or Keplerian configuration in a corneal topography system.

The mobile computing device-based corneal topography system of the present invention may be most accurately described as being a Keplerian loupe, with an aperture stop located at a hole in a Placido assembly (e.g., a Placido cone), and an image of that aperture stop located at the pupil of the mobile communication device (e.g., the image sensor of the mobile communication device). Although a Keplerian loupe may be utilized, other optical systems including Keplerian design forms or Keplerian configurations may also be utilized. Thus, the remainder of the specification may refer to the optical system described herein as an optical system including a Keplerian design form or Keplerian configuration. In this Keplerian configuration or design form, an aperture stop (hole in a Placido assembly (e.g., Placido cone) is oversized slightly, so that its image at the mobile computing device end (the exit pupil of the mobile communication device-based corneal topography system) is likewise oversized slightly, so that the entrance pupil of the mobile communication device is slightly overfilled, and as a consequence the mobile communication device entrance pupil is always used to its full diameter. This slight oversizing also desensitizes the system to slight errors in in the longitudinal position of the mobile communication device pupil.

In the design of the mobile communication device-based corneal topography system, the size of the beams at the pupil at the Placido assembly (e.g., Placido cone) (or illumination system) may be determined as a trade-off between two conflicting goals. The first goal was a desire, described earlier, of making the hole in the Placido assembly (e.g., Placido cone) small so as to minimize an unmeasurable region of a corneal surface. The second goal relates to the Lagrange Invariant of the mobile computing device-based corneal topography system and a field of view at the eye end. The Lagrange Invariant is a product of the semi-field angle at the mobile computing device with the semi-diameter of the entrance pupil of the mobile computing device. The Lagrange Invariant of the entire system cannot exceed the limitation imposed by the mobile computing device, and it is desired that the full Lagrange Invariant be used, if possible. At the eye end of the mobile computing device-based corneal topography system, the Lagrange invariant is determined by the semi-field angle of the direct view of the eye and the semi-diameter of the beam diameter at the hole in the Placido assembly (e.g., Placido cone) hole. For this mobile communication device-based corneal topography system, a solution was found in which the semi-field angle of a direct view of the eye was judged to be adequate, and the required beam size at the Placido assembly (e.g., Placido cone) hole was just slightly smaller than the maximum allowable hole size. This maximum allowable hole size was determined taking into account the maximum allowable diameter of the unmeasurable region of the cornea.

The shape of a Placido assembly (e.g., Placido cone) (illumination system) itself was chosen such that the opening at the eye end was not larger than a particular diameter. The preferred outside diameter at this end is small enough to fit in front of the eye being examined, and fit inside the nose, so as to not have the nose block even the most peripheral Placido mires. If this condition is not satisfied, then the image reflected will be characterized by what is known as a "nasal shadow," identified in FIG. 7. This is a small but not insignificant design drawback of most existing commercial corneal topography systems that make up prior art. At the same time, it was desirable that the blur in the radial direction be minimized so that the mires (which are tangential in orientation) are not excessively blurred. In the language of optical design, this requirement is that the curvature of the tangential field be matched to the shape of the Placido assembly (e.g., Placido cone). Since the shape of the Placido assembly (e.g., Placido cone) was not freely selectable, the curvature of the tangential field was adjusted using an aspheric lens in one of the lens groups. More specifically, it was one of the lenses in the group located far from the hole in the Placido assembly (e.g., Placido cone) that was made aspheric. Aspherizing one of the elements near the hole in the Placido assembly (e.g., Placido cone) hole would help control spherical aberration but would give little correction over the tangential field curvature. Accordingly, the mobile communication device-based corneal topography system described above has a novel optical train using an optical system including a Keplerian configuration or design form (such as Keplerian loupe optics) and is thus different from any other corneal topography system.

In embodiments, a mobile communication device-based corneal topography system may be mounted on and/or carried by a standard slit-lamp microscope. In some embodiments, the mobile communication device-based corneal topography system may be connected or coupled to a mounting post of slit-lamp microscope. In some embodiments, space constraints may dictate that a distance between front and rear lens of an optical system including a Keplerian configuration or design form be reduced, since the optical system may be intended to be mounted on, and carried by, a standard slit-lamp microscope. A slit lamp microscope is universally employed in offices of eye care professionals worldwide. All eye care professionals are trained in its use. In embodiments, an advantage of mounting a mobile communication device-based corneal topography system on a slit lamp microscope may be that the slit lamp's joystick may be used to finely adjust and position mobile communication device-based corneal topography system relative to an eye being studied. In embodiments, a focal length or "z-axis" is of significant importance and may need to be exactly specified in order for a mobile communication device-based corneal topography instrument to have reproducible accuracy. In embodiments, a tolerance of positional accuracy is typically +/−100 microns along a z axis in order to achieve +/−0.25 D power accuracy. By contrast, prior hand-held corneal topography systems may not achieve this accuracy due to difficulty in adjusting and/or holding the instrument within specific tolerances. Accordingly, an advantage of "piggy-backing" and/or mounting a mobile communication device-based corneal topography system onto a slit lamp microscope is that the mounting provides fine positional accuracy, while also taking advantage of an optical instrument in common use by eye care professionals globally.

In some embodiments, a mobile communication device-based corneal topography system including an optical system with a Keplerian configuration or design form may require folding of the image beam passing through the optical system or optical housing (e.g., utilizing mirrors) in order to reduce the distance between the examiner and subject. Any imaging system incorporating an optical system or optical housing including a Keplerian configuration or design form may require that a larger distance be present between an imaging lens of a camera (or image sensor) of the mobile communication device and an objective lens compared to a length of an imaging system incorporating a Galilean loupe optical system of the same or similar magnification. In some illustrative embodiments, in order to optimize optics for imaging, a small diameter object (e.g., a human cornea), a mobile communication device-based corneal topography imaging system (e.g., an optical bench or corneal topography optical housing including an optical system having a Keplerian configuration or design form such as, for example, a Keplerian loupe), may have a total distance of approximately 125 millimeters between front and rear lenses. In some embodiments, a mobile communication device-based corneal topography system utilizing an optical system including a Keplerian configuration or design form may comprise a distance of approximately 199 millimeters (or 7.8 inches) from a mobile communication device camera entrance to an outer end of a Placido illumination system. In this illustrative embodiment, these two measurements are for mobile communication device-based corneal topography systems that do not utilize mirrors to bend the image beam.

In some embodiments, by having a mobile communication device-based corneal topography system residing and/or mounted on a slit-lamp microscope, an additional constraint occurs because it may be advantageous for an eye examiner's head position to be the same height or similar relative to a head position of a subject when the examiner is using the slit lamp microscope unit. When using a slit-lamp microscope during normal slit-lamp operations, an examiner is approximately 12 to 14 inches away from the examination subject. If the mobile communication device-based corneal topography system is mounted on the slit-lamp microscope and is utilizing a relatively long telescopic optical system (e.g., such as an optical system including a Keplerian design form or Keplerian configuration without the use of mirrors to fold the image beam), this may result in the examiner being significantly further away from the examination subject. For example, an optical system including a Keplerian design form (that does not use mirrors) may have an extended distance (e.g., such as the 7.8 inch distance described above). Thus, the use of the optical system including the Keplerian design form or configuration, would result in the examiner being approximately 508 millimeters or 20 inches away from the examination subject (which is farther than the normal distance of 304 to 356 millimeters (or 12 to 14 inches) when the Examiner is utilizing the slit-lamp microscope). Such an implementation would be undesirable and uncomfortable to the examiner, due to the examiner's prior use of the slit-lamp microscope. Accordingly, it would be beneficial to include mirrors in a path of the reflected image beam in order to shorten the distance between the examiner and subject when utilizing a mobile communication device-based corneal topography system. In some embodiments, the two or more mirrors in the image path of the reflected concentric ring image may reduce a distance between the subject's cornea and the camera of the mobile communication device ranging between 50 millimeters to 165 millimeters (or 2 to 6.5 inches). In some embodiments, the two or more mirrors in the image path of the reflected concentric ring image may reduce a distance between the subject's cornea and the camera of the mobile communication device ranging between 165 millimeters to 204 millimeters (or 6.5 inches to 8 inches). In some embodiments, the corneal topography optical housing may have a length to keep a distance between the examiner's eye and the subject's eye between approximately 304 to 356 millimeters (or 12 and 14 inches). In some embodiments, the corneal topography optical housing may have a length to keep a distance between the examiner's eye and the subject's eye between approximately 254 to 381 millimeters (or 10 and 15 inches).

Figure 2D:
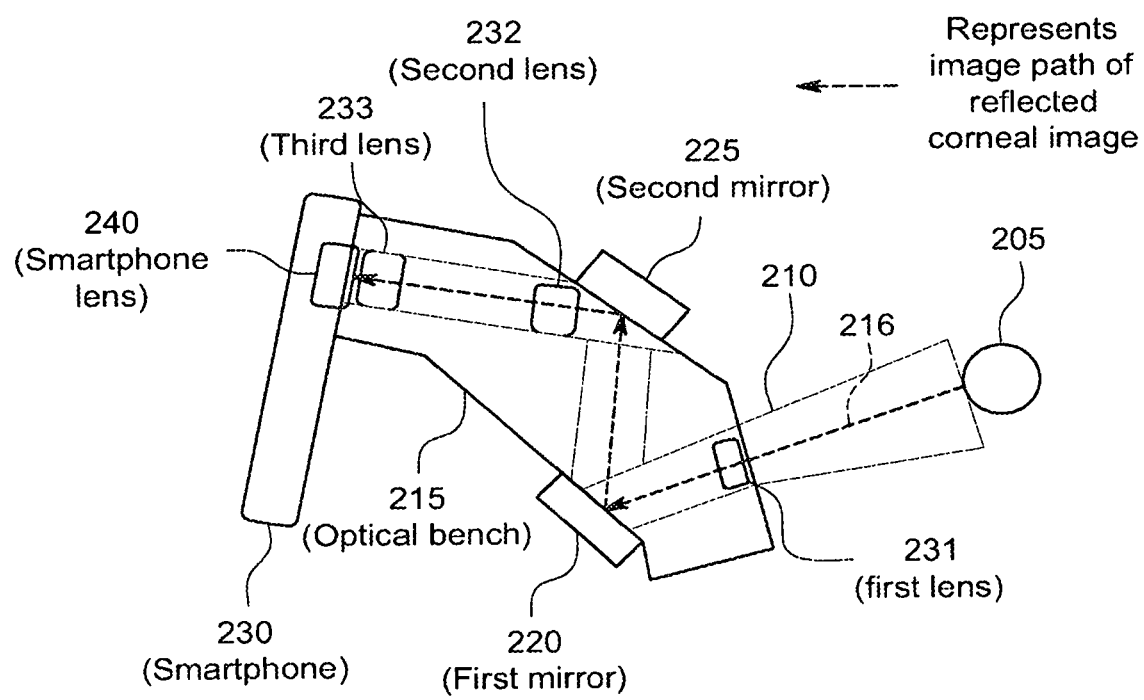
FIG. 2D illustrates a block diagram of an optical bench or corneal topography optical housing comprising two mirrors according to some embodiments.

In some embodiments, a mobile communication device-based corneal topography system may utilize two or more mirrors to fold an image beam path and thereby shorten the overall distance between front and rear lenses of the mobile computing device-based corneal topography system. FIG. 2D illustrates a block diagram of an optical bench or corneal topography optical housing coupled to two mirrors according to some embodiments. In some embodiments, a first mirror 220 may be located at a first position and a second mirror 225 may be located at a second position to fold an image beam path. The image beam path is illustrated by the arrows and reference number 210 in FIG. 2D. In some embodiments, for example, the use of two or more mirrors (e.g., mirror 220 and/or 225) to fold an image beam path reduces the overall distance between entrance pupil of the mobile communication device camera (or image sensor) and corneal vertex. In some embodiments, for example, the distance between an entrance pupil of the mobile communication device camera and the corneal vertex may be reduced to approximately 154 millimeters (or 6.1 inches), which is a reduction of approximately 45 millimeters (or 1.7 inches) from 199 millimeters (or 7.8 inches). In some embodiments, the incorporation of two or more mirrors may be unique to the disclosed mobile communication device-based corneal topography system and is not present in any prior corneal topography device.

FIG. 2D illustrates a mobile communication device-based corneal topography system comprising one or more mirrors according to embodiments. In FIG. 2D, reference number 205 may illustrate a subject's cornea. In embodiments, a mobile communication device-based corneal topography system may comprise a Placido illumination system 210, an optical bench or corneal topography housing 215 and/or a mobile communication device 230. In embodiments, a Placido illumination system may be a disc-shaped system, a cone-shaped (or conical) system, a parabolic-shaped system, or an aspheric-shaped system. In embodiments, an optical bench or corneal topography optical housing 215 may be coupled to a first mirror 220 and a second mirror 225. In embodiments, the dotted bolded line 210 may show a reflected image path of a subject's corneal image as it passes through the corneal topography optical housing or the optical bench 215. For example, the image path 210 may enter the optical bench or optical housing 215 and may be reflected by a first mirror 220 to a second mirror 225 and may exit the optical bench or corneal topography optical housing 215 into a mobile communication device camera or image sensor lens 240. By folding a projected or reflected image of a subject's corneal image (e.g., passing it through mirrors set at angles within a corneal topography optical bench 215), an overall distance between a mobile communication device camera or image sensor lens 240 and a corneal vertex may be shortened or reduced. In embodiments, an optical bench or optical housing 215 may further comprise a first lens 231, a second lens 232 and/or a third lens 233.

Although two mirrors may be utilized in a mobile communication device-based corneal topography system, in alternative embodiments, a mobile communication device-based corneal topography system having an optical system including a Keplerian design form or configuration may also comprise more than two mirrors (e.g., three mirrors, four mirrors, etc.). In an additional alternative embodiment, a mobile communication device-based corneal topography system with an optical system including a Keplerian design form or configuration may comprise one mirror that folds the projected image beam into the mobile communication device camera or image sensor. Further, in other embodiments, an optical system may include a prism, which has one or more internal reflective surfaces that are used to fold and direct a projected image beam into the pupil of a mobile communication device camera or image sensor.

FIG. 2A also illustrates a mobile communications device-based corneal topography system according to embodiments. In embodiments, an additional design consideration may be that an image of a subject's cornea on the mobile communication device's display (e.g., the reflected image) be in vertical alignment with the horizontal line connecting an examiner and an examination subject (or patient). A term of art used by movie directors and cinematographers that pertains to this may be referred to as "eye line". That is an imaginary line connecting the eyes of two actors in a scene. In a corneal topography system, an "eye-line" between an examiner and a subject has traditionally been in a horizontal plane. The "eye-line" refers to a condition where the eye of the examiner should be aligned in a horizontal plane with the eye of the subject being examined. FIG. 2A illustrates a horizontal eye line 256 between an examiner and an examination subject. In a mobile communication device-based corneal topography system where the eye-line 256 may be maintained in a horizontal plane between an examiner and subject, an examiner should not have to look up, or down, or to one side or another relative to a horizontal line of sight connecting an examiner and a subject patient. In embodiments of a mobile communication device-based corneal topography system, it may be preferable to have a corneal topography image on the mobile communication display be reasonably aligned both horizontally and vertically such that the eye-line passes through a center of a live camera image of mobile communication device display.

Figure 2E:
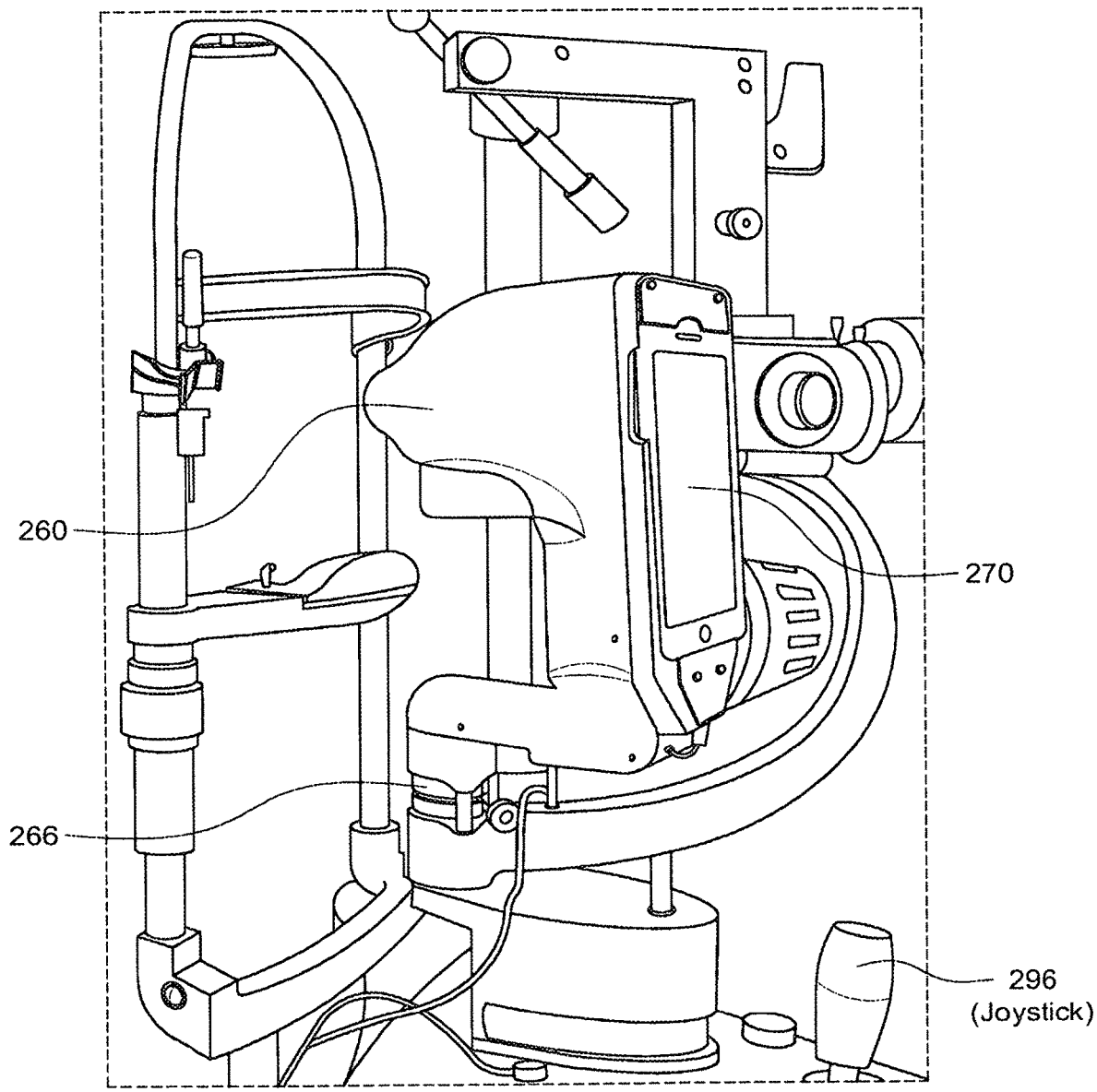
FIG. 2E illustrates a mobile-computing device-based corneal topography system attached to a slit lamp microscope according to some embodiments.

FIG. 2A illustrates an eye-line 256 between an examiner and a subject in a mobile communication device-based corneal topography system according to embodiments. FIG. 2A illustrates that a similar or common horizontal plane between an examination subject and an examiner is maintained through a Placido illumination system 267 (or illumination system 267), an eyepiece 258, an optical bench or corneal topography optical housing 260 (e.g., mirrors, optics and/or electronics), and a mobile communication device 270. In other words, the mobile communications device-based corneal topography system illustrated in FIG. 2A shows that a horizontal plane or eye-line 256 connects a center of a patient's (or subject's) eyes 281 and an examiner's (or user's) eyes 282, when an examiner's eyes 282 are looking at a center of a mobile communication device screen (or more specifically when an examiner may be looking at a center of the upper full-width square area mobile communication device screen). This allows ease-of-use for an examiner in that it maintains the same or similar horizontal plane eye-line relationship that existed when the Examiner utilized the slit-lamp microscope. In other words, the examiner is used to such a horizontal plane eye-line positioning when the examiner operates the slit-lamp microscope. In some embodiments, the mobile communication device-based corneal topography system, which is attached to the slit-lamp microscope, does not change this horizontal plane eye-line relationship. A mobile computing device-based corneal topography system may comprise a bulkhead and a slit lamp mounting plate and/or mounting assembly according to embodiments. In some embodiments, a bulkhead or positioning plate may be utilized to align and/or attach other pieces of a smartphone-based corneal topography system in place in order to enable efficient operation. In some embodiments, a bulkhead or a positioning plate may include a recess for a Placido illumination system 267 and/or eye piece 258. In some embodiments, a mounting assembly (e.g., a positioning plate may attach to an optical bench or corneal topography optical housing) may be utilized to connect to a slit lamp microscope mounting assembly. In embodiments, a mobile communication device-based corneal topography system may be attached (or piggy-backed) onto a slit-lamp microscope in order to maintain examination accuracy. With reference to FIG. 2A, in some embodiments the Z axis of the topography system comprises the optical axis of the light pattern, e.g. placido disk or concentric rings pattern or illumination pattern, and the optical axis of the imaging system. In embodiments, a corneal topography system may need +/−100 micron z-axis positional accuracy in order to have +/−0.25 Diopter accuracy in calculating accurate corneal power. Prior art (or legacy) desktop corneal topography systems incorporate their own patient head rests and a joystick-based x-y-x positioning apparatus to align and position the corneal topography system relative to a patient's eye. In some embodiments, a mobile computing device-based corneal topography system attached to a slit-lamp microscope, utilizes the slit-lamp microscope's built-in and existing x-y-z positioning system, where a roller-track and a joystick provides fine motor control of x-y-z positioning. FIG. 2E illustrates a mobile-computing device-based corneal topography system attached to a slit lamp microscope according to some embodiments. In FIG. 2E, a user or examiner may utilize a joystick 296 for fine motor control of x-y-z positioning of the coupled or connected mobile computing device-based corneal topography system. In some embodiments, the joystick 296, may move the slit lamp microscope (and thus the connected mobile communication device 270 and corneal topography optical housing 260). The use of a slit-lamp microscope in the mobile computing device-based corneal topography system takes advantage of the fact that all eye care professionals are already trained in and experienced with use of a slit-lamp microscope. In embodiments, a positioning plate or mounting assembly may be manufactured with tight tolerances to allow proper operation of a mobile communication device-based corneal topography system.

In an alternative embodiment, a mobile communication device-based corneal topography system may further comprise a fiber-optic bundle, and/or a fiber-optical receiver or transceiver. In this alternative embodiment, the fiber-optic bundle and/or receiver may communicate the reflected image beam to the camera or image sensor of the mobile communication device. In this alternative embodiment, the fiber-optic bundle may be a coherent fiberoptic bundle, as the intent is preserve the corneal image in its entirety (e.g., without image scatter, disruption of image quality, or other distortion that may be introduced by failure to preserve the exact geographic alignment of all fibers in the fiber-optic bundle relative to each other). In this alternative embodiment, other components of the mobile communication device-based corneal topography system, e.g., the Placido illumination system, the optical bench or housing (including electronics, lenses, mirrors, and/or beam splitters) and the mobile communication device, may be positioned to maintain the eye-line in a horizontal plane 256 between the examiner and the subject.

In some embodiments, a mobile computing device-based corneal topography system may comprise an optical bench or corneal topography optical housing including two or more mirrors. In some embodiments, an additional feature of utilizing two or more mirrors in the optical bench or optical housing is the ability of adjusting an angle of inclination for the two or more mirrors to cause adjustment of an image beam projected into the mobile computing device camera or image sensor to be slightly tilted relative to a vertical axis. In addition, adjusting an angle of inclination of the two or more mirrors in the optical bench or optical corneal topography housing may also allow for vertical and horizontal offset of the image beam projected into a central axis (or pupil) of the mobile communication device camera or image sensor to accommodate for a multiplicity of camera or image sensor locations on the rear surface of a mobile communication device.

Figure 3A:
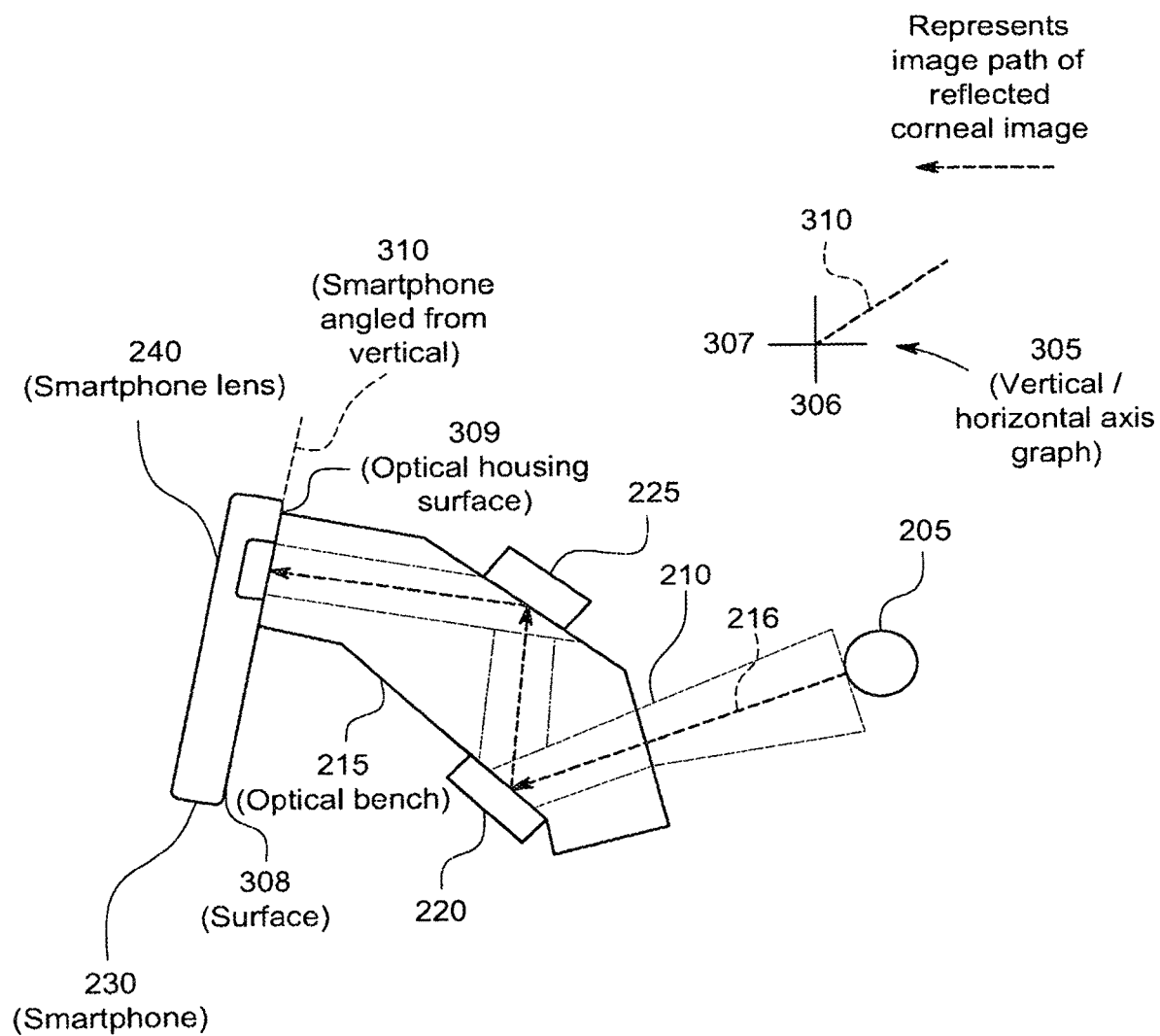
FIG. 3A illustrates a mobile computing device-based corneal topography system including two or more mirrors positioned at specific angles according to embodiments.

FIG. 3A illustrates a mobile computing device-based corneal topography system including two or more mirrors positioned at specific angles according to embodiments. In embodiments, the mirrors referenced and illustrated in FIG. 3A may be perfectly parallel, in which case the mirrors would project an image in the same plane as the patient's cornea being studied. However, it is additionally desirable to have the image projected into a mobile communication device camera or image sensor that is slightly tilted relative to a vertical axis to enhance ease-of-use by and comfort of the examiner. In some embodiments, the image projected into a mobile computing device camera or image sensor may be tilted with respect to a vertical axis at any angle. In some embodiments, for example, the image projected into the mobile computing device camera or image sensor may be titled with respect to vertical axis, for example, between 0 and 40 degrees. In some embodiments, the image projected into the mobile computing device camera or image sensor may be titled with respect to the vertical axis, for example, between 0 and 15 degrees. In embodiments, an advantage of the two-mirror design is that it may be used to offset the angle of the projected image relative to the plane perpendicular to the chief ray into the cornea being imaged. This feature is unique to the proposed mobile computing device-based corneal topography system design.

In some embodiments, a horizontal axis and a vertical axis graph is illustrated by reference number 305. In some embodiments, the horizontal axis is illustrated by reference number 306 and the vertical axis is illustrated by reference number 307. Reference number 310 (shown with respect to the vertical axis 306 of the graph 305 as well as with respect to the optical bench or optical housing 215) illustrates how both a mobile computing device surface 308 (e.g., a back surface) and an optical bench or optical housing surface 309 have an angle offset from the vertical axis. In some embodiments, by having this angular offset or angle of inclination, allows for ease-of-use by the examiner because the mobile computing display is slightly tilted and easier to read (e.g., it would be more difficult to read if the display were perpendicular to a horizontal surface, such as a table). In some embodiments, the angular offset from the vertical axis for the mobile computing device surface 308 and the optical bench or housing surface 309 may be the same or very close to the same angle. In some embodiments, the angular offset from the vertical axis for the mobile computing device surface 308 and the corneal topography optical bench or housing surface 309 may range from 0.1 to 15 degrees. In some embodiments, the angular offset from the vertical axis for the mobile computing device surface 308 and the optical bench or housing surface 309 may also range from 1 to 40 degrees. In some embodiments, the angular offset from the vertical axis for the mobile computing device surface 308 and the corneal topography optical bench or housing surface 309 may range from 1 to 10 degrees or from 2 to 8 degrees.

Figure 3B:
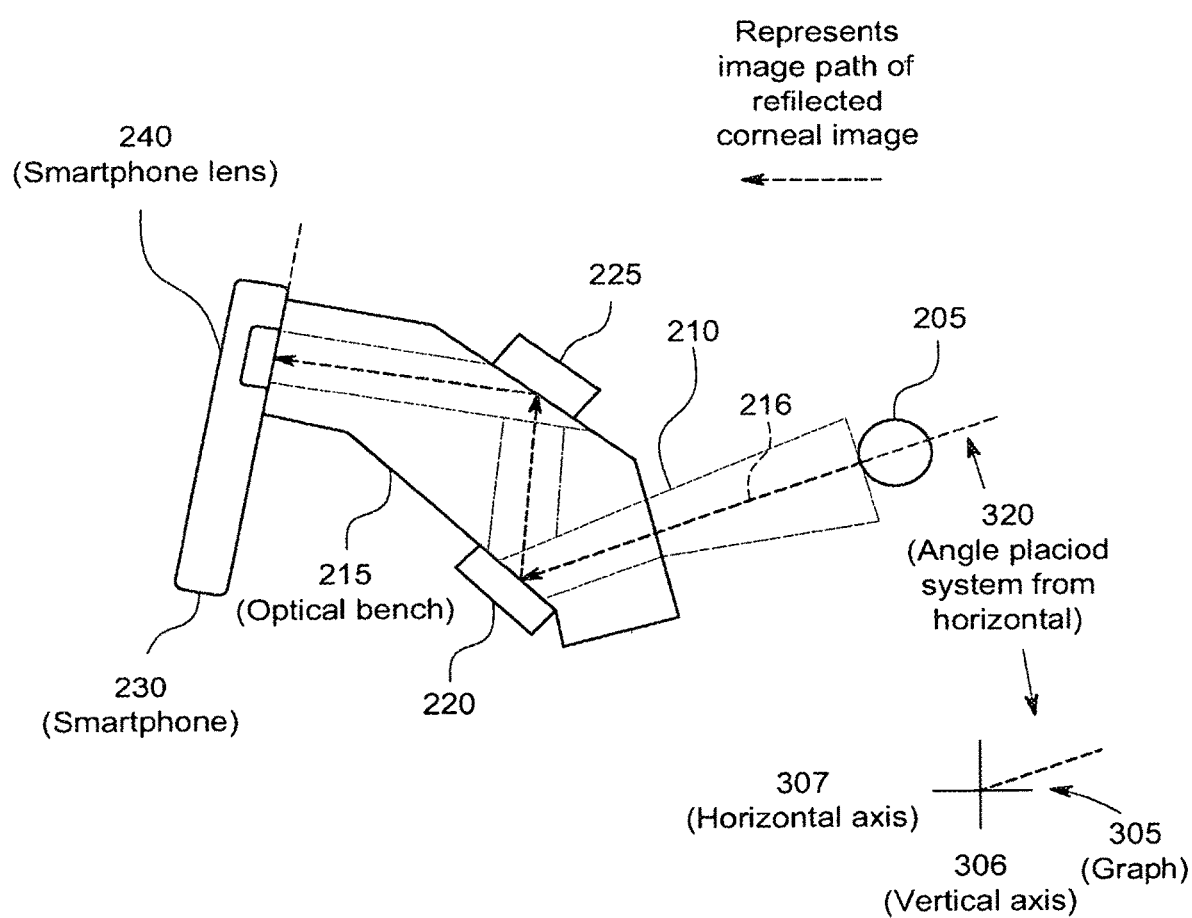
FIG. 3B illustrates a Placido illumination system and an offset from a horizontal axis according to embodiments.

FIG. 3B illustrates a Placido illumination system and an offset from a horizontal axis according to some embodiments. FIG. 3B illustrates an offset from a horizontal axis for a Placido illumination system or illumination according to some embodiments. Reference number 320 illustrates an offset from a horizontal axis for a Placido illumination system with respect to the block diagram of the mobile computing device-based corneal topography system and also with respect to a horizontal and vertical axis graph 305. In the graph, the vertical axis is identified by reference number 306 and the horizontal axis is identified by reference number 307. In embodiments, the Placido illumination system 210 having an offset from the horizontal axis allows a subject or patient to be more relaxed when undergoing an eye exam. In embodiments, having a subject look slightly downward into the Placido illumination system 210 may be slightly more comfortable for the subject or patient, rather than having the subject or patient gaze or look straight ahead (e.g., along a horizontal axis). In addition, in some embodiments, having the subject or patient look slightly downward into the Placido illumination system 210 may provide additional visibility to an upper portion of the eye. In embodiments, because the Placido illumination system may have an offset angle (or angle of inclination) from the horizontal axis, this allows the Placido illumination system to avoid contact with the supraorbital ridge of the patient or subject's eye which results in additional comfort to the subject. In some embodiments, the up-angle or offset of the Placido illumination system from the horizontal axis may be any angle. In some embodiments, for example, the up-angle or offset from the horizontal axis of the Placido illumination system may range between 1 and 40 degrees from the horizontal axis. In some embodiments, for example, the up-angle or offset from the horizontal axis of the Placido illumination system may range from approximately 0.1 to 7 degrees or may range from approximately 0.1 to 15 degrees. In some embodiments, for example, the up-angle or offset from the horizontal axis of the Placido illumination system may range from approximately 1 to 7 degrees or may range from approximately 1 to 15 degrees. In some embodiments, the subject matter described herein is the first mobile communication device-based corneal topography system that may utilize two or more mirrors to project a tilted image of the cornea as well as having a mobile computing device surface and an optical bench or housing surface slightly tilted from a vertical axis (for ease-of-use by the examiner) along with having a Placido illumination system being tilted at an up-angle or a positive offset a horizontal axis for ease-of-use by the subject or patient.

Figures 4A, 4B:
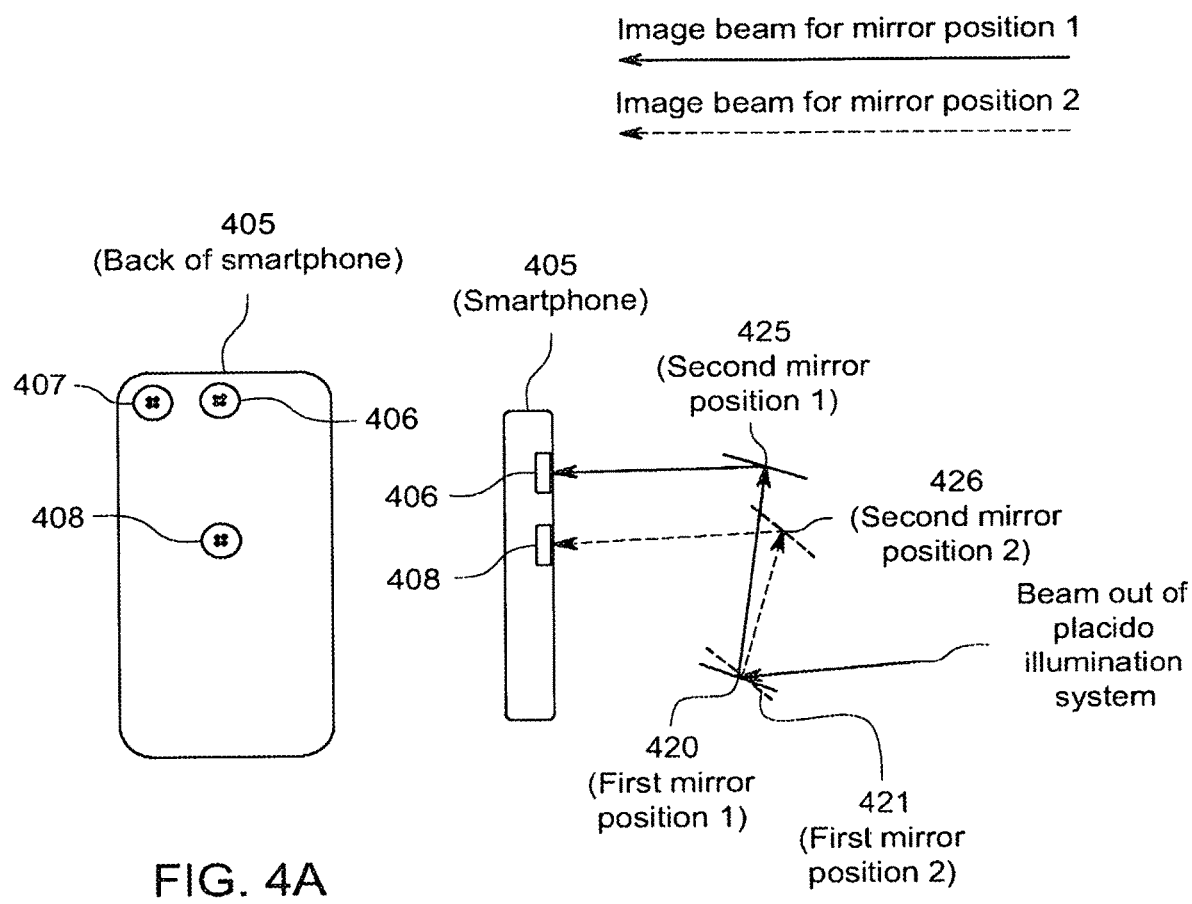
FIG. 4A illustrates different positions of mobile communication device cameras (for different mobile communication device configurations or manufacturers) on a back surface of a mobile communication device.
FIG. 4B illustrates utilization of two mirrors in a mobile communication device-based corneal topography system and how adjustment of at least one of the two mirrors may result in an offset of where a light beam enters a mobile communication device camera lens according to some embodiments.

In some embodiments, mobile communication device cameras of different platforms or manufacturers may be positioned at different locations on a mobile communication device. In some embodiments, for example, Apple iPhone 7-Plus and iPhone 8-Plus have cameras located on a top left-hand side of the back surface of the iPhone; Samsung Galaxy and other Android phones may have cameras located in a top middle of a back surface of the Android phone; and other phones may have cameras located in a center middle of a back surface of the respective phone. FIG. 4A illustrates different positions of mobile communication device cameras (for different mobile communication device configurations or manufacturers) on a back surface of a mobile communication device. In FIG. 4A, a mobile communication device 405 shows three different positions for mobile communication device cameras or image sensors (e.g., a center top position 406, a left top position 407 and a center middle position 408). The x's in each mobile communication device camera location show a potential location of where a center of a light beam enters a center axis of a mobile communication device camera. Accordingly, in some embodiments, it is desirable to utilize and/or adjust a two-mirror system in a corneal topography optical housing to reflect, transmit or point a reflected image of a subject's cornea to any camera location (e.g., top left, top center and/or middle center). In some embodiments, it is also important to preserve a relationship between the examiner eye and subject eye while being able to handle different camera positions on different mobile communication devices. In some embodiments, the two or more mirrors may be placed at different locations (e.g., different x, y, and/or z positions) within an optical bench or corneal topography housing in order to adjust to different camera positions on different mobile communication device platforms. In some embodiments, the one or more mirrors may be placed at different reflectance angles and/or different displacements or positions within an optical bench or corneal topography housing in order to adjust to different camera positions on different mobile communication device. In some embodiments, this means that different optical benches or different corneal topography housings may need to be utilized with different camera positions on the different phone platforms or manufacturers in in order to accommodate the different locations and/or different reflectance angles of the two or more mirrors.

FIG. 4B illustrates utilization of two mirrors in a mobile communication device-based corneal topography system and how adjustment of at least one of the two mirrors may result in an offset of where a light beam enters a mobile communication device camera lens according to some embodiments. In some embodiments, a beam path through the optical bench or corneal topography housing should end up entering the mobile communication device camera lens or image sensor (for the different mobile communication device camera or image sensor positions) aligned with the mobile communication device camera's or image sensor's Chief Ray or central axis. FIG. 4B illustrates a mobile communication device 405 having a camera/image sensor in a top middle position 406 and also a camera/image sensor in a center middle position 408. Please note the two positions 406 and 408 represent positions of mobile communication device cameras for different mobile communication device platforms (e.g., in most cases, a mobile communication device will not have two cameras in different positions). In some embodiments, FIG. 4B illustrates configuration and angle position of two mirrors (e.g., the first mirror in position 1 420 and the second mirror in position 1 425) and a resulting image beam path (in blue) as it enters a top center mobile communication device camera 406. FIG. 4B further illustrates adjusting an angle of reflection of two mirrors, which results in a first mirror with a second reflection angle 421 and a second mirror with a second reflection angle 426. FIG. 4B also illustrates movement or displacement of a second mirror to a second position 426 (e.g., the movement is in a downward vertical direction). FIG. 4B illustrates a resulting image beam path for a corneal reflected image as it travels through a) the first mirror (with the second deflection angle) 421; b) the second mirror 426 (with the second deflection angle and the downward displacement or movement; and c) enters a middle center positioned mobile communication device camera 408 according to some embodiments. In some embodiments, for example, movement of the second mirror 426 to a second position and second reflection angle results in their being a difference in distance between the two mirrors and this may result in the image beam losing its focus before entering the pupil of the mobile communication device camera. In some embodiments, for example, changes in a) types of lenses; b) magnification power of lens or mirrors, and/or a distance between lenses may correct the focus of the reflected image beam. FIG. 4B is meant to illustrate that it is possible to direct an image beam into different mobile communication device camera positions by changing reflection angles and/or positions of two or more mirrors in order to horizontally and/or vertically offset a projected image beam. These changes in reflection angles may also lead to changes to other parameters in an optical bench or corneal topography housing of a mobile communication device-based corneal topography system, e.g., types of lenses, number of lens, and/or magnification of lenses and/or mirrors.

Thus, FIG. 4B illustrates that if an angle adjustment is changed for the two mirrors in the optical bench or corneal topography housing, a resulting image beam entering the lens of a mobile communication device camera may be offset in a vertical (or horizontal) direction. Since FIG. 4B is a two-dimensional drawing illustrating a side view of mirrors and resulting image paths into an optical bench, the drawing cannot show a) how an adjustment of mirrors may occur in a second axis (and the resulting vertical or horizontal offset of the image beam path) and/or b) how an adjustment of mirrors in a third axis (e.g., a z-axis) may result in a tilting of the image beam path, both of which are also advantages of the two-mirror system. In addition, FIG. 4B illustrates one possible combination of mirror adjustments and many other combinations of mirror adjustments are possible. In embodiments, mirrors in an image bench may be adjusted in different x, y or z-axis positions and/or in different reflectance angles and thus may align an image path into different positioned mobile communication device cameras. The smartphone-based corneal topography system described herein is novel in that it has the ability to adapt to different camera positions on different mobile communication device platforms.

Figure 5:
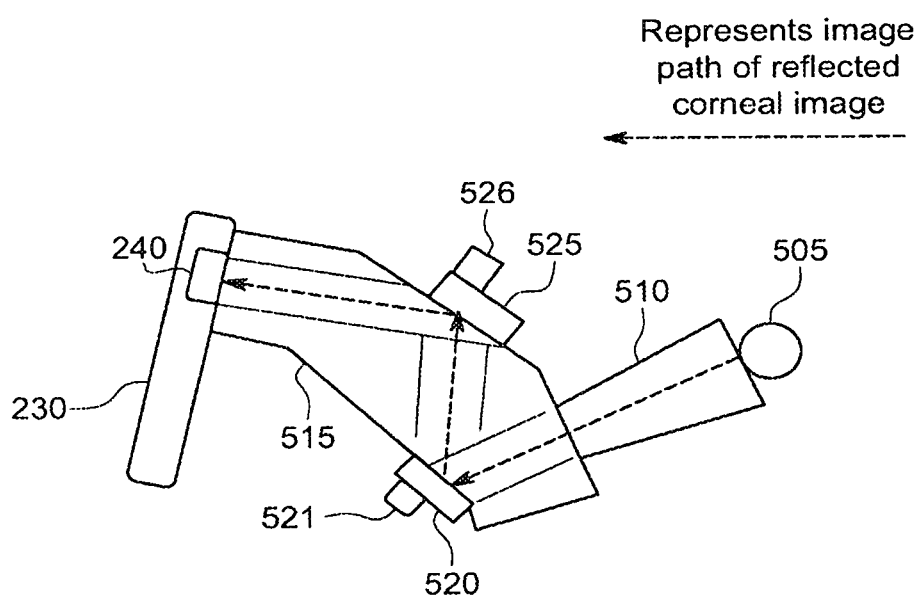
FIG. 5 illustrates corneal topography optical housing comprising one or more partial-transmittance/partial reflectance mirrors and/or a fixation target according to some embodiments.

In some embodiments, a mobile computing device-based corneal topography system may use partial-reflectance, partial-transmittance mirrors in the optical subassembly of corneal topography housing. In some embodiments, the optical subassembly of the corneal topography housing may utilize partial-reflectance or partial-transmittance mirrors in an image beam path, instead of using ideal mirrors (e.g., full reflectance mirrors). In some embodiments, if partial-reflectance, partial-transmittance mirrors (e.g., beam splitters may be partial-reflectance, partial-transmittance mirrors) are utilized, one or more fixation targets may be utilized and/or introduced as a focus target for a subject's eye during examination. In some embodiments, a fixation target may be desirable to allow an eye being examined to focus on a target appearing to reside at a far distance. In some embodiments, use of a fixation target may enable alignment of an imaging axis with a visual axis of an eye being examined. FIG. 5 illustrates corneal topography optical housing comprising one or more partial-transmittance/partial reflectance mirrors and/or a fixation target according to some embodiments. In some embodiments, a subject's eye 505 may look through a Placido illumination system 510 and through a partial reflectance/partial transmittance mirror 520 to a fixation target 521. In some embodiments, a fixation target 521 may be an LED. In some embodiments, the fixation target 521 may be colored LED, such as a red LED or a green LED.

In some embodiments, a corneal topography optical housing may also comprise a second partial-reflectance/partial-transmittance mirror (illustrated as by reference number 525 in FIG. 5). In some embodiments, a second partial-reflectance/partial-transmittance mirror 525 may add features or functionality to a mobile computing device-based corneal topography system. In embodiments, for example, a mobile computing device-based corneal topography system may further comprise an aberrometer or autorefractor subsystem 526. In embodiments, an aberrometer or autorefractor subsystem 526 may measure aberrations in a subject eye. In embodiments, the utilization of a second partial-reflectance/partial-transmittance mirror may be advantageous to gain access to an optical system or optical housing 515 to allow for analyzation of a subject' eye.

Figure 6A:
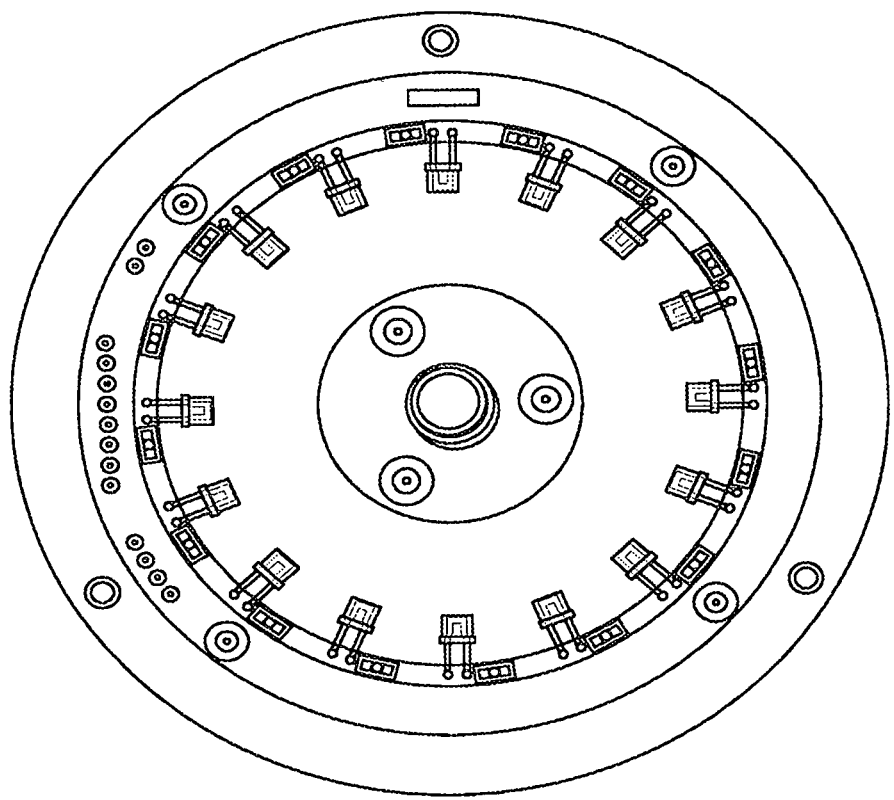
FIG. 6A illustrates a photo of a Placido disc illumination system of a Magellan Mapper according to prior art suitable for incorporation in accordance with some embodiments.
Figure 6B:
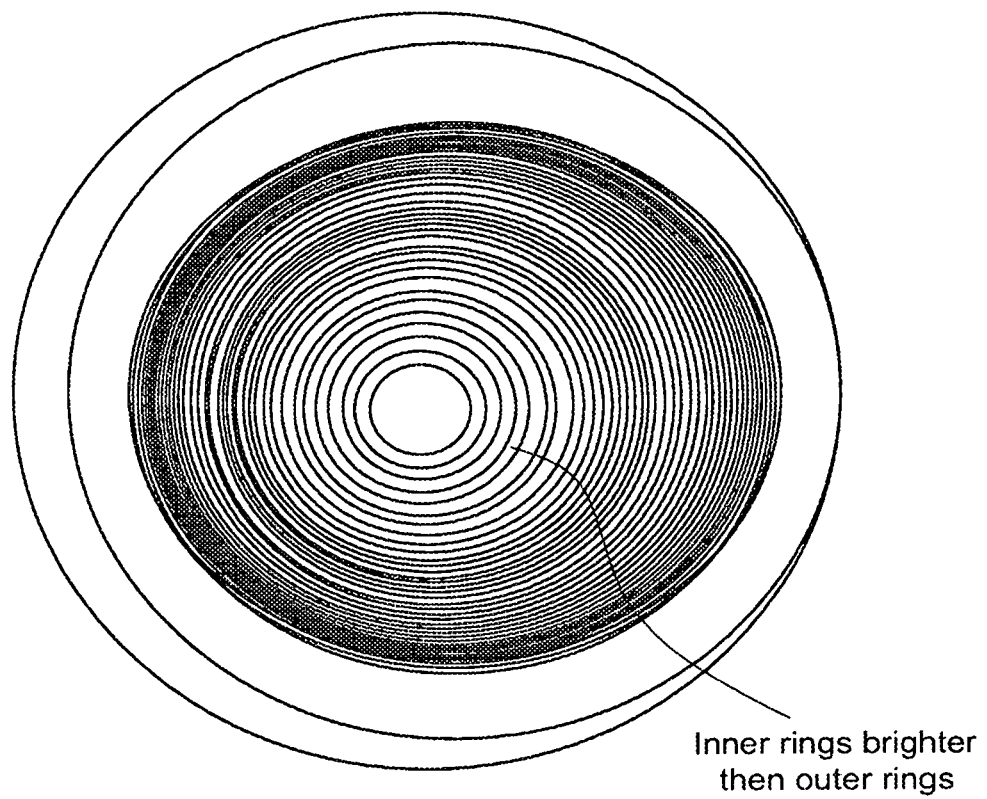
FIG. 6B illustrates a photo of a Placido disc illumination system where inner rings have a brighter appearance than the outer rings, suitable for incorporation in accordance with some embodiments t.

Corneal topography systems may illuminate a pattern onto a subject's cornea. In some embodiments, a Placido illumination system may illuminate a Placido rings pattern by providing enough light to reflect the Placido rings pattern off a subject's cornea. The reflected image may then be able to be captured and/or seen by an imaging sensor or a camera of a mobile communication device. In some embodiments, other illumination systems may be utilized other than a Placido illumination system utilizing the claimed subject matter. In prior systems, various illumination systems were utilized to provide illumination of a subject's cornea. For example, a Nidek Magellan Mapper system employs a ring array of 16 LEDs mounted just behind an end of a cone opposite an eye being studied. FIG. 6A illustrates a photo of a Placido disc illumination system of a Magellan Mapper according to prior art. Such an illumination system creates variations in brightness of Placido rings. FIG. 6B illustrates a photo of a Placido disc illumination system where inner rings have a brighter appearance than the outer rings according to the prior art. For example, as illustrated in FIG. 6B where the Magellan Mapper was used, there is a brighter appearance of the $2^{nd}$, $3^{rd}$, $4^{th}$ and $5^{th}$ rings compared to other rings generated the Magellan Mapper Placido illumination system.

In addition, in prior art corneal topography systems including the Magellan Mapper, the brightness of the rings necessary to facilitate image capture may be so bright as to cause light sensitivity, blinking, or aversion response by a patient gazing or looking into the Placido illumination system. Furthermore, the variability of brightness of Placido rings (e.g., one or more Placido rings) does not serve any constructive purpose. Brightness of illumination of the Placido rings, and color of illumination, vary substantially among embodiments of prior art. In some systems, the intensity of brightness is so great that it causes light sensitivity, blink reflex or squinting (narrowing of the lid fissure) in the eye of the patient being studied. In some legacy corneal topography systems, this brightness is so intense that the Placido illumination system may only be activated momentarily, like a camera strobe, anticipating that the subject may blink or exhibit other aversive behavior to the testing process. Clearly these are drawbacks in prior art systems that represent undesirable features.

Modern mobile communication device sensors may have markedly and/or significantly better low-light sensitivity and/or performance than older legacy camera sensor systems currently used in desktop-based corneal topography instruments. Therefore, it would be desirable to have a mobile communication device-based corneal topography system including and/or comprising a Placido illumination system with very even illumination of Placido rings, at a light level that is very comfortable to subjects being tested and/or examined.

In some embodiments, a mobile communication device-based corneal topography system having a Placido illumination system with 1) even illumination of Placido rings and 2) a low and a comfortable light level may comprise a Placido illumination system including electroluminescent ("EL") tape, Organic Light-Emitting Diode ("OLED") tape, and/or EL paints. In some embodiments, these materials may have unique characteristics suitable for the Placido illumination system of the corneal-based corneal topography system. In some embodiments, for example, an EL tape being utilized as an illumination source may provide even, "matte," and/or diffuse illumination across the EL tape's entire surface (which may be referred to as "Lambertian emittance" or "a Lambertian source"). In some embodiments, an apparent brightness of a Lambertian surface such as the EL tape to an observer is the same or very similar regardless of an observer's angle of view. In some embodiments, a surface's luminance is isotropic, and the luminous intensity obeys Lambert's cosine law. Lambertian emittance is named after Johann Heinrich Lambert, who introduced the concept of perfect diffusion in 1760.

In some embodiments, a Placido illumination system 267 may comprise a plastic cylinder. In some embodiments, for example, EL tape, may be wrapped on an outside surface or surfaces of a plastic cylinder. In embodiments, one or more power sources may apply or provide electrical current to the EL tape, and this may generate diffuse illumination (e.g., in one or several colors) on a surface of the plastic cylinder. In some embodiments, the illuminated surface of the EL tape may be directed inward. In some embodiments, the directing of the illuminated EL tape surface inward may illuminate an outside surface of the plastic cylinder. In some embodiments, the illumination of EL tape wrapped on an outside surface of the plastic cylinder may produces a quite comfortable (and/or even pleasing) resultant view of the Placido rings, as seen by a subject being examined. Accordingly, the use of EL tape, OLED tape or EL paints to illuminate Placido rings may provide an advantage of having a non-irritating light source as well as even brightness across all of the illuminated Placido rings.

Figure 6C:
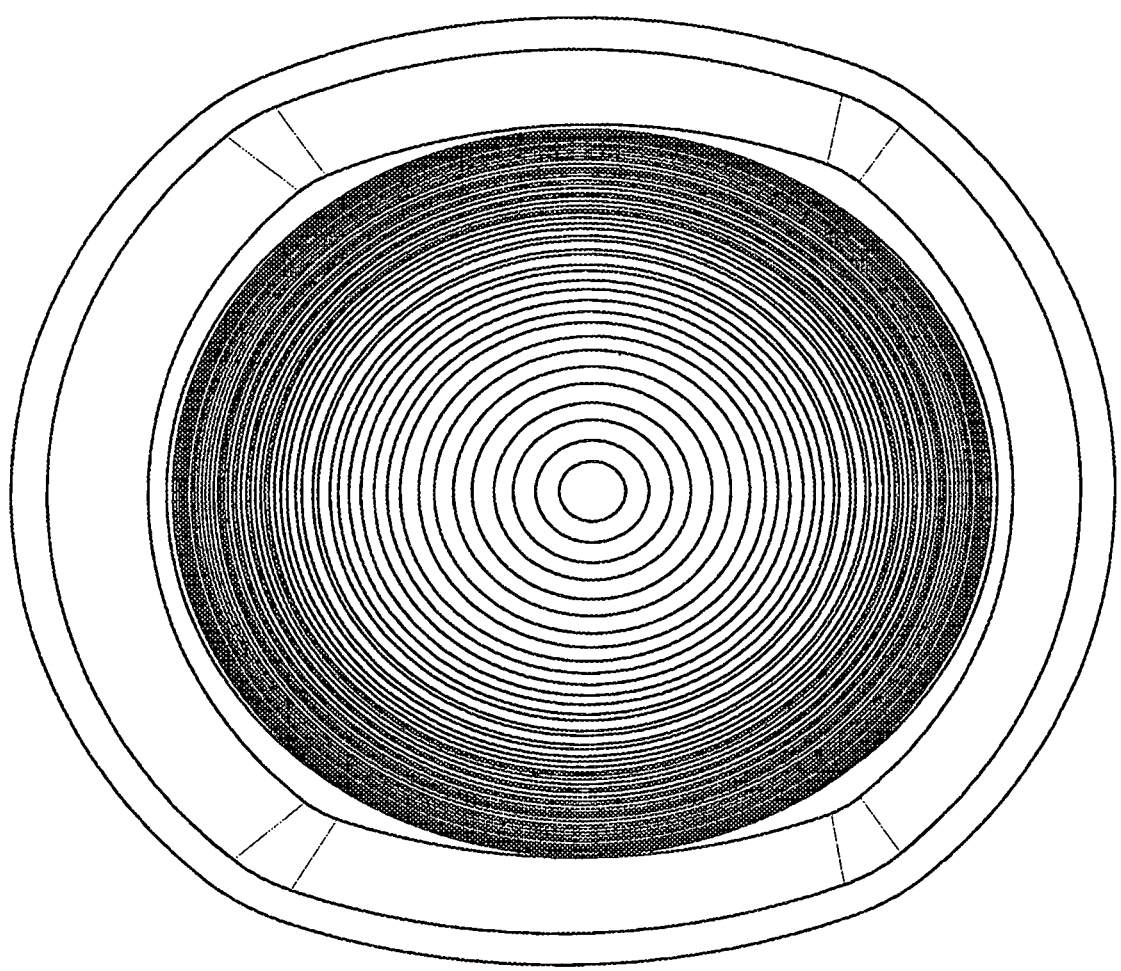
FIG. 6C illustrates even illumination of the Placido rings utilizing EL tape (e.g., the Lambertian emittance) according to some embodiments.

In some embodiments, although use of EL tape, OLED tape or EL paints is discussed above as generating a Placido concentric ring pattern, these materials may be utilized and/or illuminated to create and/or generate any type of image, which may be utilized for various ophthalmic diagnostic procedures. In embodiments, these materials may have low illumination. In some embodiments, one or more power sources may supply a low amount of current to these materials (EL tape, OLED tape, or EL paints), which generates a lower-intensity brightness. In embodiments, a lower-intensity brightness may allow testing of subjects without causing light intensity problems with subjects being examined (e.g., which addresses light sensitivity issues). As an example of utilizing EL paints or EL tapes, FIG. 6C illustrates even illumination of the Placido rings utilizing EL tape (e.g., the Lambertian emittance) according to some embodiments.

In some embodiments, EL or OLED tape may not be utilized as part of a Placido illumination system. In some embodiments, a Placido illumination system may comprise a plastic cylinder with an electroluminescent (EL) coating or layer (e.g., utilizing EL paints). In embodiments, an EL coating or layer may be applied, painted or adhered onto an inside surface and/or an outside surface of a plastic cylinder. In some embodiments, one or more power sources 261 may supply or apply power (e.g., voltage and/or current) to the EL coating or layer to evenly illuminate the EL coating or layer. In some embodiments, the even illumination of the EL coating or layer may evenly illuminate the surface of the plastic cylinder. In some embodiments, an EL coating or layer may have low power requirements than EL tape and thus not require a large amount of power. In addition, as noted above, the EL coating or layer may generate uniform illumination around a plastic cylinder of the illumination system 267. In addition, an EL coating or layer may comprise an EL paint.

There are further embodiments to enhance the brightness and viewability of the Placido illumination system. In some embodiments, a cylinder (e.g., such as a plastic cylinder) may have an interior surface rubbed and/or sanded to change a texture of the interior surface (e.g., to "rough-up" the interior surface). In some embodiments, a grit may rub or sand the interior surface of the plastic cylinder. In some embodiments, the rubbing and/or sanding may occur before application of the OLED tape, the EL tape, or the EL coating or layer. In these embodiments, the rubbing or sanding may not impair any clear portions of the cylinder. In these embodiments when the interior surface of the cylinder was rubbed or sanded, a majority of the specular reflections may be eliminated or removed. In some embodiments, these specular reflections may be present due to reflections off the black shiny interior portions of the Placido illumination system mires that existed before the rubbing or sanding.

In some embodiments, the Placido illumination system may not have an exterior shape which is actually cylindrical, but may be of an alternate shape.

In an alternative embodiment, a Placido illumination system (e.g. a Placido cone) may be modified at an eye-end to illuminate rings that may not be illuminated. In this embodiment, an outside eye-end of a Placido illumination system (e.g., a Placido cone) may be beveled to illuminate end rings (or mires) of a Placido illumination system that may be interrupted and/or not illuminated sufficiently. In this alternative embodiment, it may be difficult to apply the EL tape or OLED tape, (or EL coating or layer) all the way to a front end of the Placido illumination system because the EL or OLED tape (or EL coating or layer) may be difficult to apply and/or seal in that small of a space. In this alternative embodiment, the EL or OLED tape (or EL coating or layer) may begin to be uncomfortably perceived by the patient or subject. In this front-end region of the Placido illumination system, the end rings (or mires) may not get illuminated without the beveling of the outside eye-end of the Placido illumination system. In this alternative embodiment, the beveling of the outside eye-end of the Placido illumination system redirects light (or illumination) from the rear areas of the EL tape or OLED tape (or EL coating or layer) into the front-end rings (or mires).

In some embodiments, a Placido illumination system (e.g., a Placido cone) may have a small front end in order to allow the Placido illumination system to fit close to the subject's eye (e.g., eye being examined). Corneal topography systems incorporating such a Placido illumination system may show a "nasal shadow", which is common in desktop corneal topography systems. In some embodiments, an illumination system may generate other illumination patterns and the subject matter described herein applies to these other illumination patterns (e.g., there may be "nasal shadow" in both Placido illumination systems and/or also other illuminations systems).

Figure 7:
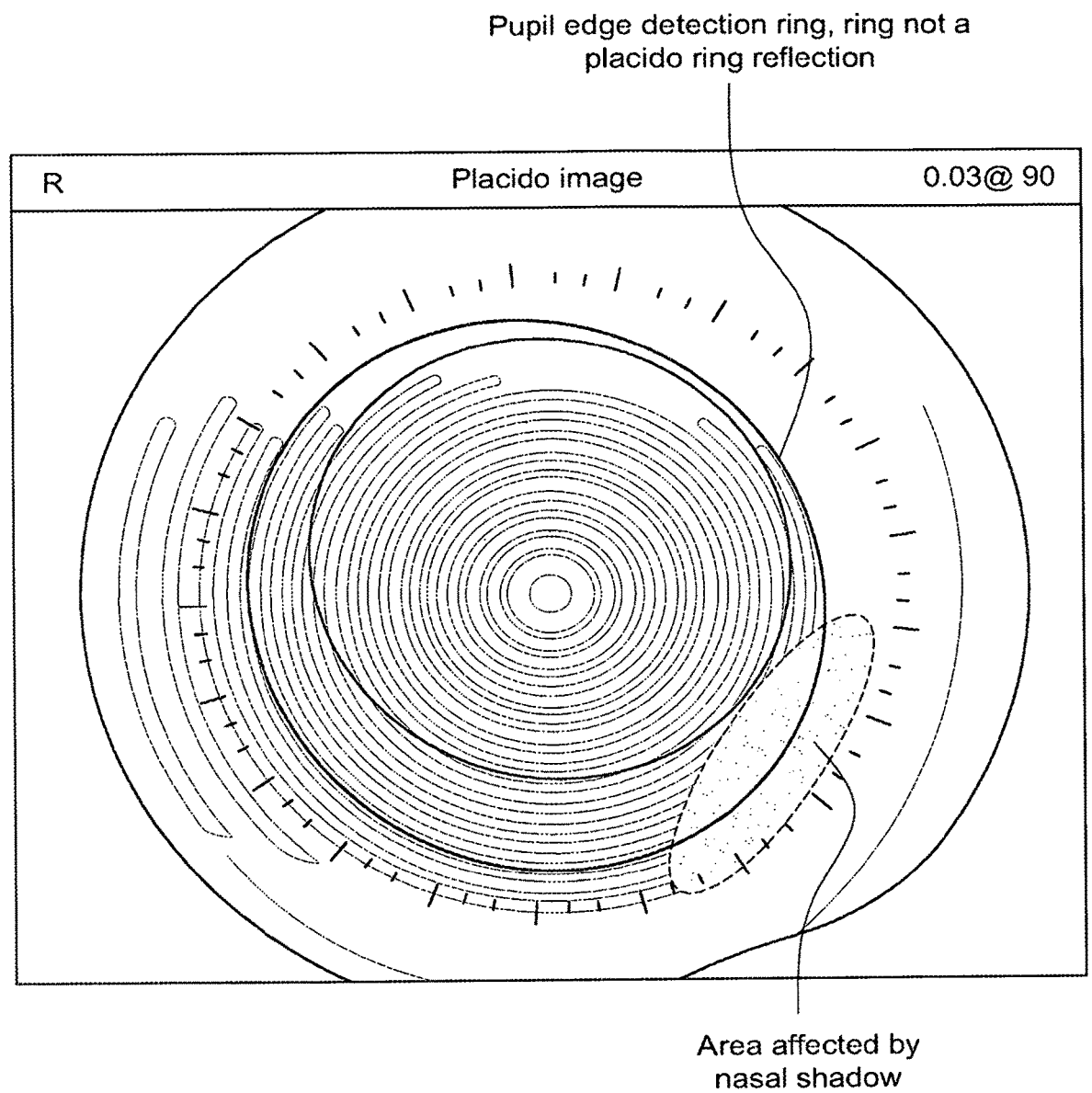
FIG. 7 illustrates impact of nasal shadow on a Placido rings projection according to some embodiments.

However, nasal shadow may present problems if not taken into consideration. Example of a study by a Nidek OPD-III corneal topography system on a right eye illustrates nasal shadow. FIG. 7 illustrates impact of nasal shadow on a Placido rings projection according to some embodiments. As illustrated in FIG. 7, ring reflections are absent in the periphery from about the 3:30 meridian clockwise down to about the 5:30 meridian. Rings are absent because a patient's or subject's nose is interfering with a projection of the illuminated rings from the Placido assembly to a cornea. In FIG. 7, a dotted oval illustrates an area that is missing concentric rings according to nasal shadow. Accordingly, the concentric rings of the Placido illumination system are not fully projected.

Accordingly, in some embodiments, it is also advantageous for a mobile communication device-based corneal topography system to enable automatic detection of whether a left eye or a right eye of a subject is being examined to minimize nasal shadow.

Figure 8A:
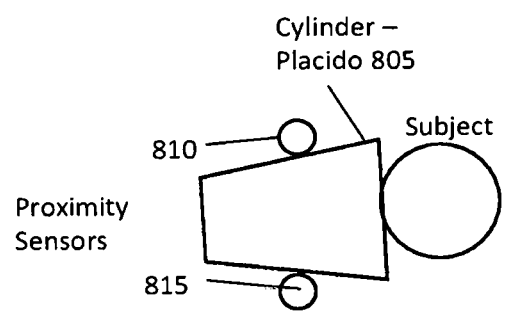
FIG. 8A illustrates a Placido illumination system comprising proximity sensors to measure whether a left eye or a right eye is being examined according to some embodiments.

In some embodiments, a mobile communication device-based corneal topography system may comprise a Placido illumination system, where the Placido illumination system may comprise a cylinder (e.g., a plastic cylinder). In some embodiments, a Placido illumination system may further comprise two or more proximity sensors, although other sensor assemblies may be used. In some embodiments, a corneal topography optical housing may comprise two or more proximity sensors. FIG. 8A illustrates a Placido illumination system comprising proximity sensors according to some embodiments. FIG. 8A illustrates two proximity sensors 810 and 815 and a Placido illumination system 805. In some embodiments, the proximity sensors 810 and 815 may be mounted on an outside surface of the plastic cylindrical housing and/or outside of the plastic cylindrical housing. In some embodiments, the proximity sensors may be mounted underneath the plastic cylindrical housing. In some embodiments, the proximity sensors may be mounted at the 4:00 and 8:00 meridians on the plastic cylinder 805 facing radially outward. In some embodiments, the proximity sensors may be mounted at ranges of the 2:30 to 5:30 meridians on a right side and a range of 6:30 to 9:30 meridians on a left side of the plastic cylinder 805 facing outward. In some embodiments, for example, on a side of a plastic cylinder 805 facing a nose of a subject, an infrared (IR) signal generated by the proximity sensor 810 may have a higher amplitude than an amplitude of the proximity sensor 815 on the opposing side (e.g., a proximity sensor not facing a nose of the subject). In some embodiments, comparator circuitry (e.g., comparators) in a mobile communication device-based corneal topography system may automatically compare signal amplitudes of the two proximity sensor 810 or 815 outputs (e.g., amplitude of IR signal) and thus can automatically determine whether the corneal system is facing or examining the right eye or left eye. Although IR signals are described herein, a triangulation method utilizing other sensor signals (having other wavelengths) may also be employed by the proximity sensors and comparator system. In some embodiments, proximity sensors 810 and 815 may utilize IR signal wavelengths/frequencies, RF signal wavelengths/frequencies, ultrasound signal wavelengths/frequencies, and/or other signal wavelengths/frequencies.

Figure 8B:
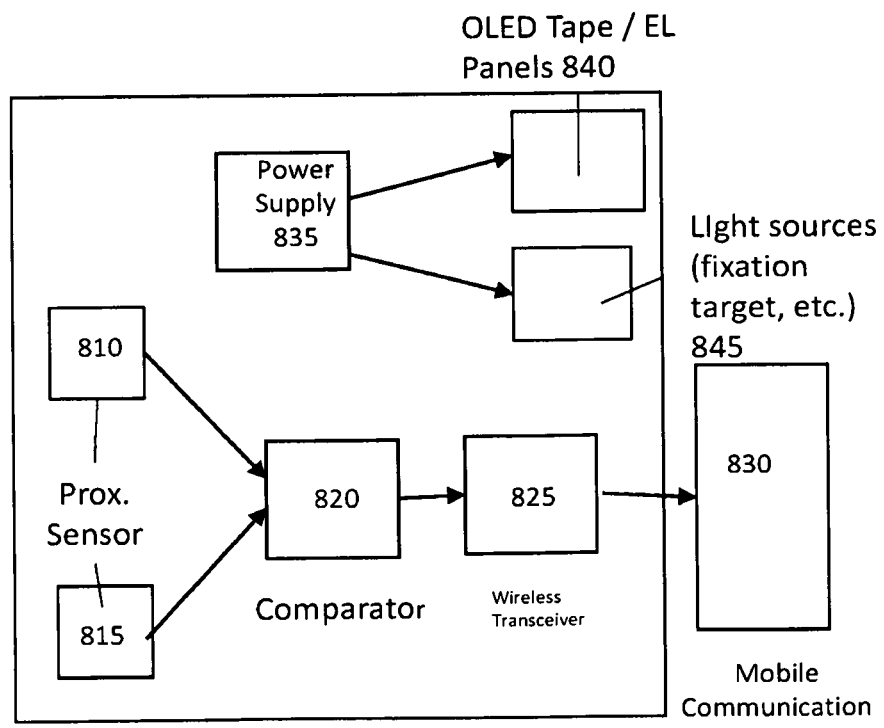
FIG. 8B illustrates a block diagram of electronic components of a mobile communication device-based corneal topography system according to some embodiments.
Figure 8C:
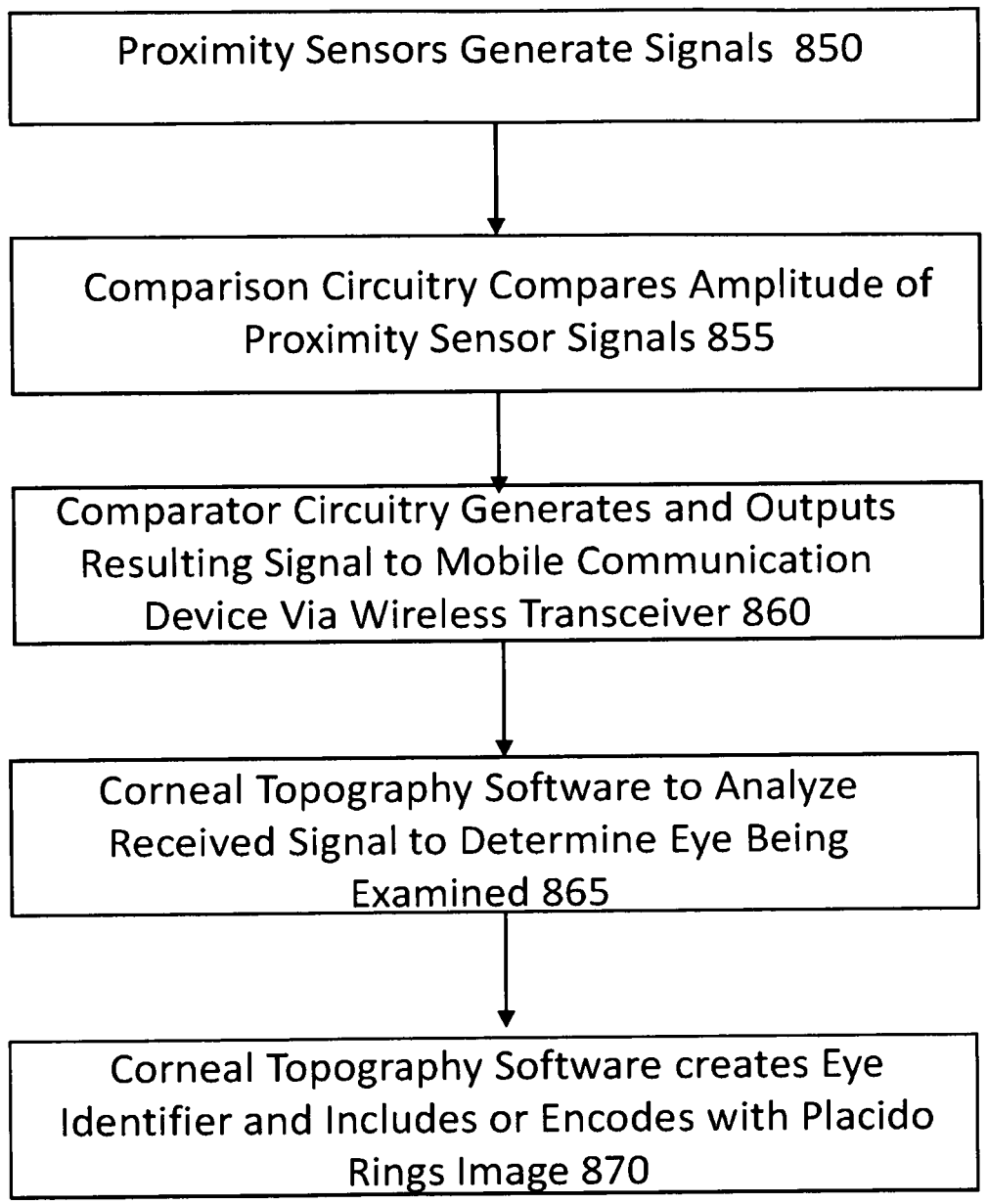
FIG. 8C illustrates a method of determining whether a right eye or a left eye is being examined by a corneal topography system according to some embodiments.

FIG. 8B illustrates a block diagram of electronic components of a mobile communication device-based corneal topography system according to some embodiments. FIG. 8C illustrates a method of determining whether a right eye or a left eye is being examined by a corneal topography system according to some embodiments. In some embodiments, in step 850, the proximity sensors 810 and 815 may generate signals as a patient is being examined. In some embodiments, in step 855, a comparator 820 (or comparator circuitry) may compare the signal amplitudes generated by the two proximity sensors 810 and 815. In some embodiments, in step 860, the comparator 820 (or other comparison circuitry) may generate an output and/or result that may be communicated (e.g., transmitted) to a mobile communication device 830 via a wireless transceiver 825. In some embodiments, a wireless transceiver 825 may be a PAN transceiver (e.g., a Bluetooth or Zigbee transceiver). In some embodiments, a wireless transceiver may be an 802.11 transceiver, (e.g., a Wi-Fi transceiver). In some embodiments, in step 865, computer-readable instructions executable by one or more processors on a mobile computing device may analyze the received amplitudes of the proximity sensor signals may generate eye identifying parameters (e.g., whether the left eye or right eye is being examined). In some embodiments, in step 870, the eye identifiers may be included within or encoded in a file containing the Placido rings image for the eye of the subject that has been studied. In addition, FIG. 8B further illustrates a power supply for a corneal topography optical housing according to some embodiments. In some embodiments, a power supply 835 may be a rechargeable and/or replaceable power supply (e.g., a battery). In some embodiments, a power supply 835 may include a battery and/or a transformer, which may provide power to proximity sensors 810 and 815, a Placido illumination system (e.g., LEDs) such as OLED tape, EL tape, or an electroluminescent coating or layer 840, a comparator or other comparison circuitry 820, a wireless transceiver 825, one or more processors 826, one or more memory devices 827 and/or other light sources 845 (e.g., a fixation target), and/or other components such as an aberrometer.

As detailed above, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor. The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step. In addition, one or more of the devices described herein may transform data, physical devices, and/or representations of physical devices from one form to another. For example, one or more of the devices recited herein may receive image data of a sample to be transformed, transform the image data, output a result of the transformation to determine a 3D process, use the result of the transformation to perform the 3D process, and store the result of the transformation to produce an output image of the sample. Additionally, or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including," "incorporating," "includes," "incorporates," and "having" (and their derivatives), as used in the specification and claims, are interchangeable with and shall have the same meaning as the word "comprising."

The processor as disclosed herein can be configured with instructions to perform any one or more steps of any method as disclosed herein.

As used herein, the term "or" is used inclusively to refer items in the alternative and in combination. As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A mobile communication device-based corneal topography system, comprising:
   an illumination system, the illumination system configured to generate an illumination pattern and to generate reflections of the illumination pattern off a cornea of a subject, wherein the illumination system is aligned along an axis of centers of the illumination pattern;

a mobile communication device, the mobile communication device comprising an image sensor, the image sensor to capture an image of the reflected illumination pattern; and a corneal topography optical housing coupled to the illumination system and coupled to the mobile communication device, wherein the corneal topography optical housing supports and aligns the illumination system with the image sensor of the mobile communication device, the corneal topography optical housing comprising an imaging system coupled to the image sensor, wherein the imaging system comprises a Keplerian configuration to magnify the image of the reflected illumination pattern being evaluated and also to decrease an optical path length between the cornea of the subject and the image sensor.

2. The mobile communication device-based corneal topography system of claim 1, wherein a surface of the mobile communication device is tilted with respect to a vertical axis to provide enhanced viewing of the reflected illumination pattern image by an examiner.

3. The mobile communication device-based corneal topography system of claim 1, wherein the imaging system comprises two or more mirrors and wherein the two or more mirrors are titled with respect to a vertical axis and/or a horizontal axis.

4. The mobile communication device-based corneal topography system of claim 1, wherein the illumination system is titled upward by an angle of inclination with respect to a horizontal axis to facilitate alignment with an eye of the subject being examined.

5. The mobile communication device-based corneal topography system of claim 1, wherein the illumination system, the corneal topography optical housing and the mobile communication device are positioned to maintain a horizontal plane of alignment between a subject and an examiner during operation of the corneal topography system.

6. The mobile communication device-based corneal topography system of claim 1, further comprising two or more proximity sensors, the two or more proximity sensors coupled to the illumination system and utilized to determine whether a left eye or a right eye of the subject is being examined.

7. The mobile communication device-based corneal topography system of claim 1, further to comprise a mounting assembly, the mounting assembly to couple the corneal topography optical housing on a slit-lamp microscope.

8. The mobile computing device-based corneal topography system of claim 1, wherein the reflected illumination pattern is a concentric rings pattern.

9. The mobile computing device-based corneal topography system of claim 1, wherein a Z axis of the corneal topography system comprises an optical axis of the illumination pattern and an optical axis of the imaging system.

10. A mobile communication device-based corneal topography system, comprising:

an illumination system, the illumination system to generate an illumination pattern, and to generate reflections of illumination pattern off a cornea of a subject;

a mobile communication device, the mobile communication device comprising an image sensor, the image sensor to capture an image of the reflected illumination pattern; and a corneal topography optical housing coupled to the illumination system and coupled to the mobile communication device, wherein the corneal topography optical housing supports and aligns the illumination system with the image sensor of the corneal topography optical housing, and the corneal topography optical housing includes an imaging system coupled to the image sensor, the imaging system comprising a Keplerian configuration to magnify the image of the reflected illumination pattern being evaluated and also to decrease an optical path length between the cornea of the subject and the image sensor, the corneal topography optical housing coupled to two or more mirrors, the two or more mirrors being positioned in an image path of the reflected illumination pattern image and located in front of a position of the image sensor of the mobile communication device.

11. The mobile communication device-based corneal topography system of claim 10, wherein a length of an image path is greater than a physical distance from the cornea to the image sensor.

12. The mobile communication device-based corneal topography system of claim 10, the two or more mirrors to reduce a distance between the subject's cornea and the image sensor of the mobile communication device to between 50 millimeters (2 inches) and 165 millimeters (6.5 inches).

13. The mobile communication device-based corneal topography system of claim 10, the two or more mirrors to reduce a distance between the subject's cornea and the image sensor of the mobile communication device to between 165 millimeters (6.5 inches) and 216 millimeters (8.5 inches).

14. The mobile communication device-based corneal topography system of claim 10, the corneal topography optical housing having a length to keep a distance between the examiner's eye and the subject's eye between 254 to 381 millimeters (10 to 15 inches).

15. The mobile communication device-based corneal topography system of claim 10, wherein a surface of the mobile communication device is tilted between 1 to 10 degrees with respect to a vertical axis.

16. The mobile communication device-based corneal topography system of claim 10, wherein an optical axis of the illumination pattern is aligned with an optical axis of the image sensor.

17. The mobile communication device-based corneal topography system of claim 10, wherein the angle of inclination of the illumination system ranges from 1 to 7 degrees relative to a horizontal axis.

18. The mobile communication device-based corneal topography system of claim 10, wherein a surface of the mobile communication device is titled with respect to a vertical axis and a center of the eye is centered on a display of the mobile communication device when a subject's eye is at a correct distance from an examiner's eye.

19. The mobile communication device-based corneal topography system of claim 10, further comprising an autorefractor, wherein a second mirror of the two or more mirrors is a partial reflectance, partial transmittance mirror, wherein the aberrometer is positioned behind the second mirror to measure aberrations in a subject's eye.

* * * * *